United States Patent [19]

Labrie et al.

[11] Patent Number: 5,364,847
[45] Date of Patent: * Nov. 15, 1994

[54] INHIBITORS OF SEX STEROID BIOSYNTHESIS AND METHODS FOR THEIR PRODUCTION AND USE

[75] Inventors: Fernand Labrie; Yves Merand, both of Quebec, Canada

[73] Assignee: Endorecherche, Canada

[*] Notice: The portion of the term of this patent subsequent to Apr. 20, 2010 has been disclaimed.

[21] Appl. No.: 966,112

[22] Filed: Oct. 22, 1992

Related U.S. Application Data

[63] Continuation of Ser. No. 322,154, Mar. 10, 1989, abandoned.

[51] Int. Cl.$^5$ .................. A61K 31/56; A61K 31/58; C07J 31/00
[52] U.S. Cl. ...................... 514/182; 514/169; 514/172; 514/176; 514/177; 514/178; 514/874; 514/964; 552/526; 552/536; 552/623
[58] Field of Search .................. 514/182, 874, 964; 552/526, 536, 623

[56] References Cited

U.S. PATENT DOCUMENTS

| | | | |
|---|---|---|---|
| 2,875,199 | 2/1959 | Cella et al. | 260/239.5 |
| 3,562,260 | 2/1971 | Ruggieri et al. | 552/626 |
| 3,975,413 | 8/1976 | Pierdet et al. | 260/397.1 |
| 3,995,060 | 11/1976 | Neri et al. | 424/324 |
| 4,055,641 | 10/1977 | Benson et al. | 424/242 |
| 4,094,994 | 6/1978 | Schönenberger | 424/341 |
| 4,096,253 | 6/1978 | Wachter et al. | 552/536 |
| 4,139,638 | 2/1979 | Neri et al. | 424/324 |
| 4,161,540 | 7/1979 | Neri et al. | 424/324 |
| 4,191,759 | 3/1980 | Johnston et al. | 424/242 |
| 4,235,893 | 11/1980 | Brodie et al. | 424/243 |
| 4,307,111 | 12/1981 | Crawley | 424/278 |
| 4,386,080 | 5/1983 | Crossley et al. | 424/209 |
| 4,472,382 | 9/1984 | Labrie | 424/177 |
| 4,536,516 | 8/1985 | Harper et al. | 514/514 |
| 4,547,493 | 10/1985 | Teutsch et al. | 514/179 |
| 4,623,660 | 11/1986 | Richardson | 514/514 |
| 4,634,696 | 1/1987 | Teutsch et al. | 514/179 |
| 4,636,505 | 1/1987 | Tucker et al. | 514/256 |
| 4,659,516 | 4/1987 | Bowler et al. | 360/397.5 |
| 4,659,695 | 4/1987 | Labrie | 514/15 |
| 4,732,912 | 3/1988 | Pilgrim et al. | 514/510 |
| 4,751,240 | 6/1988 | Bowler et al. | 514/510 |
| 4,760,053 | 7/1988 | Labrie | 514/15 |
| 4,760,061 | 7/1988 | Edwards et al. | 560/138 |
| 4,822,528 | 4/1989 | Colombo et al. | 260/397.3 |
| 4,833,135 | 5/1989 | Edwards et al. | 514/212 |
| 4,874,754 | 10/1989 | Nique et al. | 514/178 |
| 4,904,661 | 2/1990 | Pilgrim et al. | |
| 4,943,566 | 7/1990 | Nedelec et al. | 514/179 |
| 5,021,414 | 6/1991 | Pilgrim et al. | 514/237.5 |
| 5,023,234 | 6/1991 | Labrie et al. | 514/15 |
| 5,064,813 | 11/1991 | Labrie et al. | 514/15 |
| 5,204,337 | 4/1993 | Labrie et al. | 514/182 |

FOREIGN PATENT DOCUMENTS

| | | |
|---|---|---|
| 0011372 | 5/1980 | European Pat. Off. . |
| 138504 | 4/1985 | European Pat. Off. . |
| 0138504 | 4/1985 | European Pat. Off. . |
| 0160508 | 11/1985 | European Pat. Off. . |
| 0163416 | 12/1985 | European Pat. Off. . |
| 0166509 | 1/1986 | European Pat. Off. . |
| 0285383 | 10/1988 | European Pat. Off. . |

(List continued on next page.)

OTHER PUBLICATIONS

Wakeling et al., CA 106:149712y (1987).

(List continued on next page.)

*Primary Examiner*—Marianne M. Cintins
*Assistant Examiner*—Kimberly R. Jordan
*Attorney, Agent, or Firm*—Ostrolenk, Faber, Gerb & Soffen

[57] ABSTRACT

Certain steroidal and non-steroidal compounds have been found to inhibit androgen and estrogen formation. Such inhibition may aid in the reduction of the activity of these hormones and may be useful in the treatment of diseases where, for example, inhibition of androgen or estrogen acitivity is desired. Preferred inhibitors also possess antiestrogenic activity, thus providing the advantage of a double inhibitory action both on estrogen formation and on estrogen action.

11 Claims, 3 Drawing Sheets

FOREIGN PATENT DOCUMENTS

| | | |
|---|---|---|
| 3242894 | 5/1984 | Germany . |
| 3339295 | 5/1984 | Germany . |
| 0083545 | 8/1981 | Luxembourg . |
| 0137542 | 9/1967 | New Zealand . |
| 0142112 | 6/1968 | New Zealand . |
| 0208441 | 1/1988 | New Zealand . |
| 0214798 | 9/1988 | New Zealand . |
| 0214998 | 6/1989 | New Zealand . |
| 0222103 | 8/1989 | New Zealand . |
| 0223262 | 8/1989 | New Zealand . |
| 8601105 | 2/1986 | WIPO . |

OTHER PUBLICATIONS

Wakeling et al., CA 109:104945x (1988).
Wakeling and Bowler, *J. Steroid Biochem.* vol. 30, No. 1–6, pp. 141–147, 1988.
Séguin et al., Mol. Cell. Endocrinol. 21: pp. 37–41 (1981).
Dobernauer, et al. "Advanced Male Breast Cancer . . . ", Cancer 62:474–478, (1988).
Landvatter et al., J. Med. Chem. pp. 1300–1307, (1982).
Weatherill et al., J. Steroid Biochem. 30: No. 1–6 pp. 263–266 (1988).
Labrie et al., Genitourinary Cancer ISBN 0-89838-83-0-9, 1987 pp. 157–200.
Von Angerer, et al., J. Med. Chemistry, 1984, 27, 1439–1447.
Wagner et al., 21 Symposium Dstch. Ges. Endodrin. Abstract 52 (1975).
Weiss et al., Angew. Chem./Internat. Edit/vol. 12 (1973) No. 10, p. 841.
New Zealand Patent Office Journal No. 1293 Jan. 1987, #206745.
New Zealand Patent Office Journal No. 1321 vol. 78; #213652 (1985).
New Zealand Patent Office Journal No. 1342 vol. 80 Issue No. 2, #222883 (1991).
Santen et al., p. 1375 No. A22 Abstract (1988).
Mobbs et al., No. 1410 abstract (1988).
Klingmuller et al., p. 1395 No. A62 abstract (1988).
Lefebvre et al., 2-Mammalian Hormones, vol. 99, No. 99; 188132r (1983).
New Zealand Patent Office Journal No. 1266 Abstract No. 201536 (1982).
Doorenbos et al., J. Pharm. Sciences 60:88 1971 pp. 1234–1235.
Heiman et al., J. Med. Chem. 23 (1980) pp. 994–1002.
Fevig et al., Steroids 51 (1988) pp. 471–497.
Mouridsen et al., Cancer Treatment Review 5: pp. 131–141 (1978).
Musto et al. Endocrine Research Comm.; vol. 4, No. 2, 1977 pp. 147–157.
Solo, et al., Steroids vol. 40, No. 6, Dec. 1902, pp. 603–614.
Alan Liss, Inc., "The Prostate" vol. 5, 1984 pp. 123–140.
K. E. H. Gohring et al., World Patent Information vol. 11, No. 1, 1989; pp. 5–10.
Bucourt et al., J. Biol. Chem. 253: 8221 1978.
Auchus et al., Biochem., (1986) 25: 7295–7300.
Auchus et al., (1988) J. Biol. Chem., 263: 11640–11645.
Auchus et al., (1989) Steroids 53: 77–96.
Bhatnagar et al., (1978) J. Biol. Chem. 253: 811–815, 1978.
Chin et al., J. Biol. Chem. 255: 3660–3664 (1980).
Chin et al., J. Biol. Chem. 250: 7682–7686 (1975).
Klijin et al. J. Steroid Biochem. 20 (6B) (1984) p. 1381.
Thomas et al. J. Bio. Chem. 258: (1983) pp. 11500–11504.
Furr et al., J. Endo. 113, No. 3, vol. 113, Jun. 1987 pp. R7–R9.
Jordon et al., Endocrinolgoy 124, No. 4, (1989).
Important Advance in Oncology, Eds: Devita, Hellman and Rosenberg, pp. 193–217 1985.
Salman et al., J. Steroid Biochem, 33, No. 1, pp. 25–31, 1989.
Green et al., Nature, 320: pp. 134–139, Mar. 1986.
Levesque et al., J. Med. Chem, 34, pp. 1624–1630, 1991.
Wakeling, et al. J. Endocr., 112, R7–R10, 1987.
Tora et al. EMBO 8 (7) pp. 1981–1986 (1989).
Doorenbos et al. J. Pharm. Sciences 62, 4, pp. 638–640 (1973).
Doorenbos et al., J. Pharm Sciences 63, 4 pp. 620–622 (1974).
Nayfeh et al., Steroids 14:3 pp. 269–283 (1969).
Levy et al. Biochemistry, 26: 2270–2279 (1987).
McDonald et al., J. Pharm and Exper. Therapeutics 244: pp. 428–431 (1987).
Murdock et al. Biochem. 27: 4432–4438, (1988).
Pittaway D. E. Contraception 27: 431–436, (1983).
Poulin et al., Cancer Res. 46: 4933–4937, (1986).
Strickler et al., J. Biol. Chem. 256: 316–321, (1981).
Thomas et al., J. Biol. Chem. 258: 11500–11504 (1983).
Thomas et al., J. Steroid Biochem. 25: 103–108 (1986).
Thomas et al., J. Biol. Chem. 258: 1587–1590 (1983).
Tobias et al., J. Biol. Chem. 257: 2783–2786 (1982).
Warren et al., Am. J. Obstet. Gynecol. 129: 789–794 (1977).

OTHER PUBLICATIONS

Lubahn et al., Proc Natl Acad. Sci. 86: 9534–9538 (1989).
Lubahn et al., Science 240: 327–330 (1988).
Luthy et al., J. Steroid Biochem, 31: (5) pp. 845–882 (1988).
Macaulay et al., J. Steroid Biochem. 26: (5) 535–588 (1988).
Simard et al. Mol. Cell. Endocrinology 44: pp. 775–783 1988.
Neumann et al., Clinics in Oncology 1: (1) pp. 41–64 (1982).
Bull et al., J. Chem. Soc. Chem. Comm. pp. 451–453 (1986).
Cooke, Jr., Tetrahedron Letters No. 22, pp. 1983–1986 (1973).
Chang et al., Biochemistry 21: (17) pp. 4103–4109 (1982).
Gibson et al., Angew Chem. Intl. Edit. vol. 7 (12) pp. 919–930 (1968).
Grunwell et al., Steroids 27: (6) pp. 759–771 (1976).
Labrie et al., Satellite Symposium, 7th Intl. Congress of Endocrino, abstract form.
Lee et al., J. Androl. 1981; 2: 293–299.
Labrie et al., J. Steroid Biochem 19: No. 1 pp. 999–1007. (1990).
Labrie et al. The Prostate 4: 579–594 (1983).
Blickenstaff et al., 46: (4 and 5) pp. 889–901 (1985).
Habenicht et al., The Prostate 11: 313–326 (1987).
Gyorki et al., J. Steroid Biochem 25: (3) pp. 355–358 (1986).
Farnsworth, Invest. Urology 6: (4) pp. 423–427 (1969).
Neri et al., J. Stero. Biochem., 6: pp. 815–819 (1975).
Plante et al., J. Steroid Biochem, vol. 13; (1) pp. 61–64 (1988).
Raucher et al. J. Org. Chem 1981, 46, 3558–3559.
Redding et al., Proc. Natl. Acad. Sci. USA vol. 80 pp. 1459–1462 (1983).
Schally et al., Cancer Treatment Reports vol. 68 (1) pp. 281–288 (1984).
Schwarz et al., Organic Synthesis Collective vol. 3: 332–333 (1988).
Voigt et al., Endo 92 (4) pp. 1216–1222, (1973).
Wang et al., Can J. Chem. 65: pp. 2727–2731 (1987).
U.S. Application: 322,154, Filed Mar. 10, 1989, Labrie.

INHIBITORS OF SEX STEROID BIOSYNTHESIS AND METHODS FOR THEIR PRODUCTION AND USE

This is a continuation of application Ser. No. 07/322,154 filed on Mar. 10, 1989, now abandoned.

BACKGROUND OF THE INVENTION

This invention relates to methods for inhibiting sex steroid formation and in particular to novel methods for inhibiting androgen and estrogen formation in vivo in warm-blooded animals, including humans.

For a number of years, there has been research for compounds which can efficiently inhibit androgen and/or estrogen formation (e.g. enzyme inhibitors) or for compounds which may suppress androgen or estrogen action (steroid antagonists), without casuign adverse effects to healthy tissues.

Recently, estradiol derivatives bearing a carboxyalkyl substituent at the 7α-position maintained their affinity for the estrogen receptor when linked via their carboxy group to agarose or polyacrylamide resin for affinity chromatography purification of the estrogen receptor (Bucourt et al., J. Biol. Chem. 253: 8221, 1978). It was subsequently found that certain 7α-substituted derivatives of estradiol possess antiestrogenic activity (Bowler et al., 1985, Eur, Patent Application 0138504; Wakeling and Bowler, J. Steroid Biochem. 30: 141–147, 1989).

Non steroidal compounds bearing a similar aliphatic side chain have also been found to possess antiestrogenic activity (U.S. Pat. No. 4,732,912).

Some steriod derivative, such as especially 16-methylene estradiol and 16-methylene estrone, have been described as inhibitors of 17α-hydroxysteroid dehydrogenase activity (Thomas et al., J. Biol. Chem. 258: 11500, 1983).

Prior art methods have not been completely effective in inhibiting sex steriod synthesis while avoiding undesirable side effects.

SUMMARY OF THE INVENTION

Figure 1:
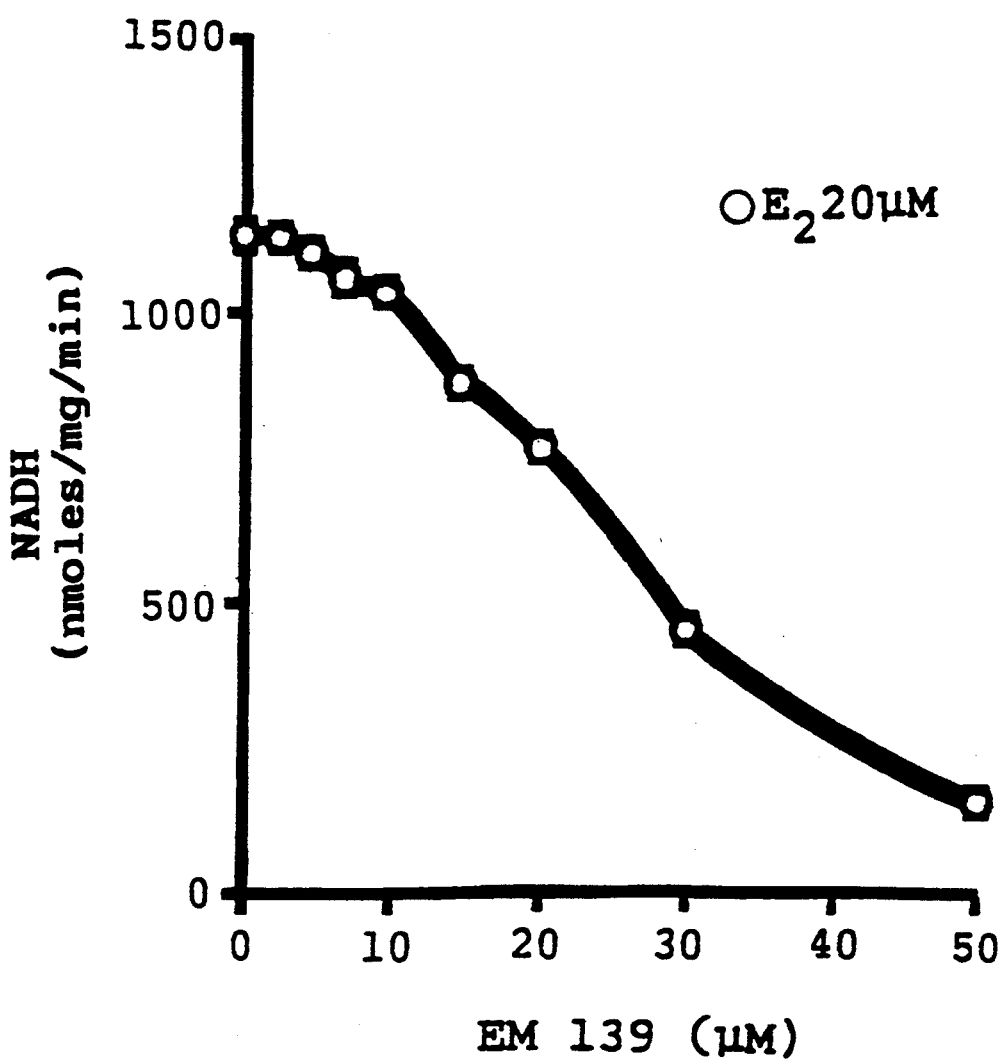
FIG. 1 is a graph showing the inhibitory effect of N-butyl, N-methyl-11-(16′α-chloro-3′,17′β-dihydroxy estra-1′,3′,5′(10′)-trien-7′α-yl) undecanamide ("EM 139") on 17β-hydroxysteroid dehydrogenase activity at different concentrations.

It is an object of the present invention to provide methods for effective inhibition of sex steroid formation.

It is another of the invention to provide methods for effective inhibition of estrogen biosynthesis in vivo in warm-blooded animals.

It is another object of the invention to provide methods for effective inhibition of androgen biosynthesis in vivo in warm-blooded animals.

It is another object of the invention to provide noval compositions for inhibition of sex steroid formation.

It is another object of the invention to provide composiions which act both as sex hormone antagonists and as inhibitors of sex hormone production, and methods for utilizing such compositions.

It is another object of the invention to provide inhibitors of sex hormone formation which are cost efficient to produce.

These and other objects may be achieved by providing a method for inhibiting sex steroid formation in a warm-blooded animal, including man, by administering a therapeutically effective amount of a compound of the formula:

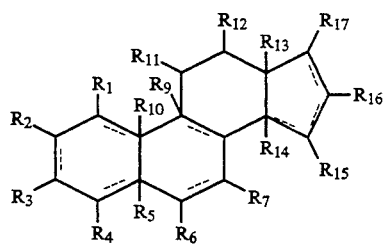

wherein the dotted lines represent optional double bonds; wherein the A-ring is optionally aromatic;

wherein $R_1$, $R_2$ and $R_4$ are independently selected from the group consisting of hydrogen, hydroxyl, alkylsulfonyl (lower) alkoxy, arylsulfonyl (lower) alkoxy, halogen, lower alkyl, lower alkoxy, lower alkylsilyl, amino and nitro;

wherein $R_3$ is selected from the group consisting of hydrogen, hydroxyl, halogen, lower alkyl, methoxy, ethoxy, propoxy, hydroxyethoxy, lower alkoxy, acetoxy, propionyloxy, butyryloxy, oenanthoyloxy, cypionoyloxy, trans-4-n-butyl-cyclohexanecarbonoyloxy, ($C_2$-$C_{20}$) alkanoyloxy, lower alkoxy carbonyloxy, carboxy, ($C_3$-$C_{20}$) alkenoyloxy, ($C_3$-$C_{20}$) alkynoyloxy, ($C_7$-$C_{10}$) aroyloxy or a divalent common species formed jointly by $R_{3(\alpha)}$ and $R_{3(\beta)}$, said divalent commond species being selected from the group consisting of =O, =S, =NR$_{36}$ or =NOR$_{36}$ wherein $R_{36}$ is hydrogen or lower alkyl;

wherein $R_5$ and $R_{10}$ are absent or selected from the group consisting of hydrogen and lower alkyl;

wherein $R_5$ is selected from the group consisting of hydrogen, halogen, lower alkyl, amino and nitrile;

wherein $R_7$ is in α position and is hydrogen, hydroxyl, halogen, lower alkyl, lower alkoxy, lower alkylsilyl, amino, nitrile, nitro, nitroso, alkylsulfonyl, arylsulfonyl, lower alkylamino, dilower alkylamino, or is represented by the formula $A^1$-[Y—$A^{11}$]$_u$—X—$R_{11}$, wherein:

u is an integer from 0 to 5; wherein $A^2$ and $A^{11}$ may be the same or different and are selected from the group consisting of a bond, straight- or branched-chain alkylene, straight- or branched-chain alkynylene, straight- or branched-chain alkenylene, and fluoro-substituted analogs of the foregoing, wherein $A^1$ and $A^{11}$ together have a total of from 3 to 30 carbon atoms, and Y is selected from the group consisting of —O—, —S—, —Se—, —SO—, —SO$_2$—, —CO—, —NR$_{22}$—, —SiR$_{22}$R$_{22}$—, —CR$_{22}$OR$_{22}$—, —NR$_{22}$CO—, —NR$_{22}$CS—, —CONR$_{22}$—, —CSNR$_{22}$—, —COO—, —COS—, —SCO—, —CSS—, —SCS—, —OCO— and phenylene ($R_{22}$ being hydrogen or lower alkyl); $R_{21}$ is selected from the group consisting of hydrogen, straight- or branched-chain lower alkyl, lower alkenyl or lower alkynyl, ($C_3$-$C_7$) cycloalky, halogeno (lower) alkyl, halogeno (lower) alkyl, carboxy (lower) alkyl, (lower) alkoxycarbonyl (lower) alkyl, ($C_6$-$C_{10}$) aryl, ($C_7$-$C_{11}$) arylalkyl, di(lower) alkylamino (lower) alkyl and fluorosubstituted analogs of the foregoing, and whrein X is —$CONR_{23}$—, —$CSNR_{23}$—, —$NR_{24}CO$—, —$NR_{24}CS$—, —$NR_{24}CONR_{23}$—,

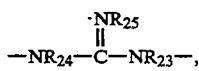

—$SO_2NR_{23}$—, —CSS—, —SCS—, —$NR_{23}$—, $(NO)R_{23}$—, —$(PO)R_{23}$—, —$NR_{24}COO$—, —$NR_{24}SO_2$—, —S—, —SO— or —$SO_2$—, (where $R_{23}$ is selected from the group consisting of hydrogen, lower alkyl, and a species which, together with $R_{21}$, forms a saturated or unsaturated heterocyclic ring having at least one nitrogen atom and, aptionally, a second heteroatom selected from the group consisting of oxygen, sulfur, silicon, selenium, nitrogen and fluoro-substituted analogs of the foregoing, and where $R_{24}$ is hydrogen or lower alkyl) wherein $R_{25}$ is hydrogen, nitrile or nitro) ($XR_{21}$ may form a tetrazole ring);

wherein $R_{11}$ is selected from the group consisting of hydrogen, lower alkyl, lower alkenyl, lower alkynyl, ($C_5$-$C_{10}$) aryl, alkylsulfonyl, arylsulfonyl, a substituted 5-to-7 member heterocyclic ring having at least one heteroatom (selected from oxygen, sulfur, silicon, selenium, nitrogen), —$(CH_2)_5W$ (wherein W is nitrile, hydroxyl, azido, nitroso, nitro, thionitrile, halogen, alkylsulfonyl or arylsulfonyl, and S is an integer from 1 to 6), $OR_{26}$ (wherein $R_{26}$ is hydrogen, lower alkyl or ($C_6$-$C_{10}$) arly), $DR_{27}$ (wherein D is —Se—, —$NR_{26}$, —S— or —O—, and $R_{27}$ is hydrogen, lower alkyl), =O, =S, =Se, =$NR_{26}$ (wherein $R_{26}$ is hydrogen or lower alkyl;

wherein $R_{12}$ and $R_{13}$ are independently hydrogen or lower alkyl; wherein $R_{14}$ is selected from the group consisting of hydrogen, hydroxyl, nitrile, nitro, nitroso, halogen, lower alkyl, lower alkoxy, lower alkyseleno, lower alkylamino or diloweralkylamino; or $R_{14}$ and $R_{15}$ together are —$CH_3$—, —CHX—, —$CX_3$—, (X=halogen, carboxyl or alkoxycarbonyl), —O—, —S—, —Se—, >N-CN, >$NR_{39}$ and >$NCO_3R_{29}$ wherein $R_{29}$ is hydrogen or lower alkyl;

wherein $R_{15}$ is selected from the group consisting of hydrogen, hydroxyl, nitro, nitroso, halogen, lower alkyl, lower alkenyl, lower alkynyl, lower alkoxy, lower alkylseleno, lower alkylamino, di(lower) alkylamino, nitrile, azido, arylseleno, $AXR_{21}$, $A_1$-$[Y-A^{11}]_u$-X-$R_{21}$ or $R_{15}$ and $R_{16}$ together are —$CH_2$—, —CHX—, —$CX_2$—, (X=halogen, carboxyl or alkoxycarbonyl), —O—, —S—, —Se—, >N-CN, >$NR_{29}$ and >$NCO_2R_{29}$ wherein $R_{29}$ is hydrogen or lower alkyl;

wherein $R_{16}$ is selected from the group consisting of hydrogen, nitroso, halogen, lower alkyl, carboxyl, lower alkoxy, lower alkylseleno, lower alkylamino, nitrile, azido, arylseleno, lower alkylseleno, di(lower) alkylamino, $AXR_{21}$, or $A^1$-$[Y-A^{11}]_u$-X-$R_{21}$, $R_{15(\alpha)}$ and $R_{16(\beta)}$ together are =$CG_2$, where G is hydrogen, halogen, lower alkyl, lower alkenyl, lower alkynyl, nitrile, alkoxycarbonyl, alkylcarbonyl and carboxyl);

wherein $R_{17(\alpha)}$ is selected from the group consisting of hydrogen, hydroxyl, lower alkyl halogeno (lower)alkyl, $AXR_2$, $A^1$-$[Y-A^{11}]_u$X-$R_{21}$, $B^1$-T-$R_{30}$ wherein:

$B^1$ is straight- or branched-chain ($C_1$-$C_{12}$) alkylene, ($C_2$-$C_{12}$) alkynylene, ($C_2$-$C_{12}$) alkynylene, ($C_2$-$C_{12}$) alkenylene; T is —O—, —$NR_{31}$, —Se—, —S— or S—S and $R_{30}$ and $R_{31}$ are inependently hydrogen, lower alkyl, or $R_{30}$ and $R_{31}$, together are ($C_3$-$C_7$) cycloalkyl, ($C_5$-$C_7$) cycloalkenyl, ($C_3$-$C_7$) cycloalkyl or ($C_5$-$C_7$) cycloalkenyl having one or more hydrogen atoms replaced by halogen atoms, —HC=$CHR_{32}$ and —C≡$CR_{33}$ wherein:

$R_{32}$ and $R_{33}$ are independently hydrogen, halogen, tri(lower) alkylsily, carboxyl, carbonyl, lower alkoxy, nitrile, sulfinyl lower alkyl, $AXR_{21}$, $A^1$-$[Y-A^{11}]_u$-X-$R_{21}$ or a species represented by the formula:

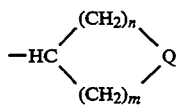

a wherein n and m are independently 0 to 6 and Q is —Se—, —$SiH_2$—, —S—, —O— —or $NR_{34}$— wherein $R_{34}$ is hydrogen, lower alkyl or ($C_1$-$C_7$) alkanoyl;

or a species represented by the formula:

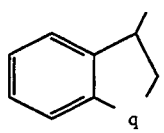

b wherein q is —$CH_2$—, —S—, —O— or —$NR_{35}$- wherein $R_{35}$ is hydrogen or lower alkyl;

wherein $R_{17(\beta)}$ is preferably selected from the group consisting of hydrogen, hydroxyl, halogen, 1-oxo-2-propynyl, 1-hydroxy-2-propynyl, alkoxy, ($C_1$-$C_7$) alkanoyloyloxy, ($C_3$-$C_7$) alkenoyloxy, ($C_3$-$C_7$) alkynoyloxy, alkenyloxy, cycloalkenyloxy, 1-alkyloxyalkyloxy, 1-alkyloxy cycloalkyloxy, alkylsilyloxy and a divalent common species formed jointly by $R_{17(\alpha)}$ and $R_{17(\beta)}$, said divalent common species being selected from the group consisting of =O, =S, =$NR_{36}$ or =$NOR_{36}$ wherein $R_{36}$ is hydrogen or lower alkyl.

The invention further provides a method for inhibiting sex steroid formation in a warm-blooded animal, including man, by administering a therapeutically effective amount of a compound of the formula:

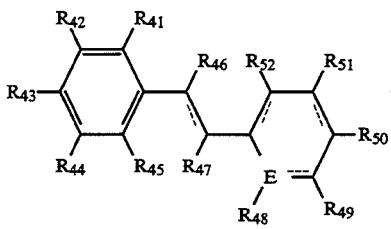

II

As used herein, the terms $R_{41}$, $R_{42}$, ..., $R_{52}$ refer to substituents whose locations on the phenylethyl frame work is illustrated in formula II where the dotted lines represent an optional double bond of Z or E configuration. Unless specifically designated to the contrary, the carbon bearing substituents may have either R or S stereochemistry. In some embodiements, the optional double bonds are not present. When the optional double bond are not present, $R_{46}$ and $R_{47}$ may each represent two independently-selected substituents. In certain preferred embodiment, a salt of the specified compounds may be used. Molecular structures set forth herein may be substituted or unsubstituted at any position where substituents are not specifically defined. Those carbon atoms having substituents defined may optionally be further substituted by a second substituent; wherein E is absent, methylene or ethylene. wherein $R_{41}$, $R_{45}$, $R_{46}$, and $R_{53}$ are independently selected from the group consisting of hydrogen, hydroxyl, halogen, lower alkyl, lower alkoxy, alkylsulfonyl lower alkoxy, arylsulfonyl lower alkoxy, lower alkylsilyl, amino, nitro, nitrile and nitroso. wherein $R_{43}$, $R_{44}$, $R_{49}$ and $R_{51}$ are independently selected from the group consisting of hydrogen, hydroxyl, halogen, lower alkyl, lower alkoxy, alkylsulfonly lower alkoxy, arylsulfonyl lower alkoxy, lower alkylsilyl, amino, nitrile, nitro, nitroso, axido, lower alkylamino, dilower alkylamino, $AXR_{21}$, $Y_{47}$-$A^1$[Y-$A^1$]$_u$-X-$R_{21}$, $A^1$-[Y-$A^{11}$]$_u$—X—$R_{21}$ wherein:

A is straight- or branched-chain ($C_1$-$C_{10}$) alkylene, ($C_2$-$C_{10}$) alkenylene, ($C_2$-$C_{30}$) alkynylene or fluoro-substituted analogs of the foregoing; u is an integer from 0 to 5; wherein $A^1$ and $A^{11}$ may be the same or different and are selected from the group consisting of a bond, straigh- or branched-chain alkylene, straight- or branched-chain alkynylene, straight- or branched-chain alkenylene, and fluoro-substituted analogs of the foregoing, wherein $A^1$ and $A^{11}$ together have a total of from 3 to 30 carbon atoms, and Y is selected from the group consisting of —O—, —S—, —Se—, —SO—, —$SO_2$—, —CO—, —$NR_{22}$—, —$SiR_{22}R_{22}$—, —$CR_{22}OR_{22}$—, —$NR_{22}CO$—, —$NR_{22}CS$—, —$CONR_{22}$—, —$CSNR_{22}$—, —COO—, —COS—, —S-CO—, —CSS—, —SCS—, —OCO— and phenylene ($R_{22}$ being hydrogen or lower alkyl); $R_{21}$ is selected from the group consisting of hydrogen, straight- or branched-chain lower alkyl, lower alkenyl or lower alkynyl, ($C_3$-$C_7$) cycloalkyl, halogeno (lower) alkyl, carboxy (lower) alkyl, (lower) alkoxycarbonyl (lower) alkyl, ($C_5$-$C_{10}$) aryl, ($C_7$-$C_{11}$) arylalkyl, di(lower) alkylamino (lower) alkyl and fluoro-substituted analogs of the foregoing, and wherein X is —$CONR_{23}$—, —$CSNR_{23}$—, —$NR_{24}CO$—, —$NR_{24}CS$—, —$NR_{24}CONR_{23}$—, $$-NR_{24}-\overset{\overset{NR_{25}}{\|}}{C}-NR_{23}-,$$

—$SO_2NR_{23}$—, —CSS—, —SCS—, —$NR_{23}$—, (NO)$R_{21}$—, —(PO)$R_{23}$—, —$NR_{24}COOO$—, —$NR_{24}SO_2$—, —S—, —SC— or —$SO_2$—, (where $R_{23}$ is selected from the group consisting of hydrogen, lower alkyl, and a species which, together with $R_{21}$, forms a saturated or unsturated heterocyclic ring having at least one nitrogen atom and, optionally, a second heteroatom selected from the group consisting of oxygen, sulfur, silicon, selenium, nitrogen and fluoro-substituted analogs of the foregoing, and where $R_{24}$ is hydrogen or lower alkyl) wherein $R_{25}$ is hydrogen, nitrile or nitro) ($XR_{21}$ may form a tetrazole ring);

wherein $R_{43}$ and $R_{50}$ are independently selected from the group consisting of hydrogen, hydroxyl, halogen, lower alkyl, methoxy, ethoxy, propoxy, hydroxyethoxy, lower alkoxy, lower alkoxy carbonyloxy, carboxyl, acetoxy propionyloxy, butyryloxy, oenanthoyloxy, cypionyloxy, trans-4-n-butyl-cyclohexanecarbonoyloxy, ($C_1$-$C_{20}$) alkanoyloxy, ($C_3$-$C_{20}$) alkenoyloxy, ($C_3$-$C_{20}$) alkynoyloxy, ($C_7$-$C_{11}$) aroyloxy and alkylsilyloxy;

wherein $R_{46}$ and $R_{47}$ are independently selected from the group consisting of hydrogen, amino, lower alkylamino, dilower alkyl amino, nitro, nitrile, nitroso, halogen, lower alkyl, lower alkenyl, lower alkynyl, halogeno lower alkyl, halogeno loweralkenyl, halogeno lower alkynyl, alkyl sulfonyl, aryl sulfonyl, a substituted 5-to-7 member heterocyclic ring having at least one heteroatom (selected from oxygen, sulfur, silicon, selenium, nitrogen), —(CH$_2$)$_s$V (wherein V is nitrile, hydroxyl, azido, nitroso, alkoxy, nitro, thionitrile, halogen, alkyl sulfonyl or aryl sulfonyl and s is an integer from 1 to 6), a moiety of the formula:

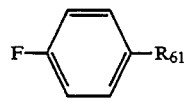   c wherein:
F is absent or selected from the group consisting of alkyl, carbonyl or carboyxl, wherein the phenyl ring may be halogenated, wherein $R_{51}$ is selected from the group consisting of hydrogen, hydroxyl, halogen, lower alkenyl, lower alkynyl, nitrile, nitro, nitroso or $X_{46}$ (CH$_2$)$_n$$Y_{46}$ ($X_{46}$ being selected from the group consisting of —O—, —S—, —Sa—, —SO—, —$SO_2$— and —CO—, and $Y_{46}$ being from the group consisting of hydroxyl, amino, monoalkyl amino, dialkyl amino, dimethyl N-oxide, N-aziridyl, guanidino, N-pyrrolidino, N-piperidino, N-methylpiperazino, N-morpholino and alkoxy, and n being an integer from 1 to 6).

$AXR_{21}$, $Y_{47}$-$A^1$-[Y-$A^{11}$]$_u$—X—$R_{21}$ wherein A, $A^1$, $A^{11}$, X, Y, $Y_{47}$ are defined previously for $R_{42}$, $R_{44}$, $R_{49}$ and $R_{51}$ $R_{46}$ and $R_{47}$ may also be a species which in combination with another substituent from formula III, forms a moiety selected from the group consisting of —CH$_2$—, —CHX—, —CX$_2$— (X being halogen, carboxyl or alkoxycarbonyl), —O—, —S—, —Se—, >N-CN, >NR$_{29}$ and >NCO$_2$R$_{29}$ (R$_{29}$ being hydrogen or lower alkyl), lower alkylene, —(CH$_2$)$_r$O(CH$_2$)$_s$—, —(CH$_2$)$_s$—, —(CH$_2$)$_r$Se(CH$_2$)$_s$—, —(CH$_2$)$_r$SO(CH$_2$)$_r$SO(CH$_2$)$_s$—, —(CH$_2$)$_r$SO$_2$(CH$_2$)$_s$—, —(CH$_2$)$_r$CO(CH$_2$)$_s$—, —(CH$_2$)$_r$NR$_{22}$(CH$_2$)$_s$—, —(CH$_2$)$_r$SiR$_{22}$R$_{22}$ (CH$_2$)$_s$— and —(CH)$_2$$_r$CR$_{22}$OR$_{22}$(CH$_2$)$_{2s}$— (wherein $R_{22}$ being hydrogen or lower alkyl, r and s being independent integers from 0 to 3), a moisty of the formula:

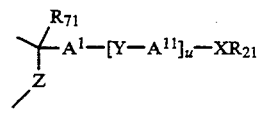   d whrein:

Z is absent or is selected from the group consisting of lower alkylene, halogeno lower alkylene, —(CH$_2$)$_n$O—, —(CH$_2$)$_n$S—, —(CH$_2$)$_n$Se—, —(CH$_2$)$_n$SO—, —(CH$_2$)$_n$SO$_2$—, —(CH$_2$)$_n$CO—, —(CH$_2$)$_n$NR$_{22}$—, —(CH$_2$)$_n$SiR$_{22}$R$_{22}$— and —(CH$_2$)$_n$CR$_{22}$OR$_{22}$—, n eing an integer from 3, and R$_{71}$ being selected from a group consisting of hydrogen, hydroxyl, halogen, lower alkyl, lower alkoxy and lower alkylsil;

the formula:

>N—A$^1$[Y-A$^{11}$]$_u$—X—R$_{11}$ wherein:

N is nitrogen atom and A$^1$, Y, A$^{11}$, u, X and R$_{21}$ are defined as above.

The invention further provides a method for inhibiting sex steroid formation in a warm-blooded animal, including man, by administering a therepeutically effective amount of a compound of the formula:

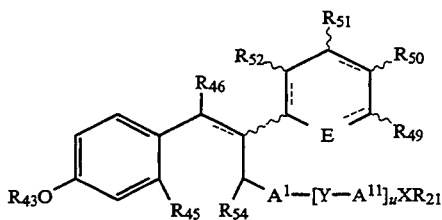

III wherein the dotted lines represent optional double bonds; wherein E is absent, methylene or ethylens; wherein R$_{43}$ is selected from the group consisting of hydrogen, alkyl, acetyl, propionyl, butyryl, oenanthoyl, cypionoyl, trans-4-n-butylcyclohexanecarbonoyl, (C$_1$-C$_{20}$) alkanoyl, (C$_3$-C$_{20}$) alkenoyl, (C$_3$-C$_{20}$) alkynoyl and (C$_7$-C$_{11}$) aroyl; wherein R$_{46}$ is selected from the group consisting of hydrogen, halogen, amino, lower mono- or dialkylamino, nitro, nitrile, nitroso, lower alkyl, lower alkenyl, lower alkynyl, halogeno analogs of the foregoing; a substituted 5- to 7-member heterocyclic ring having at least one heteroatom (selected from oxygen, sulfur, silicon, selenium, nitrogen) —(CH$_2$)$_s$ V (wherein V is nitrile, hydroxyl, azido, nitroso, alkoxy,-nitro, thionitrile, halogen, alkyl sulfonyl, aryl sulfonyl and s is an integer from 1 to 6) and the formula:

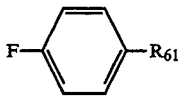

c wherein:

F is absent or selected from the group consisting of alkyl, carbonyl and carbonyl; wherein the phenyl ring may be halogenated, wherein R$_{61}$ is selected form the group consisting of hydrogen, hydroxyl, halogen, lower alkyl, lower alkenyl, lower alkynyl, nitrile, nitro and nitroso wherein R$_{45}$ and R$_{54}$ are independently selected from the group consisting of hydrogen and lower alkyl or R$_{45}$ and R$_{54}$ together from a moiety selected from the group consisting of (CH$_2$)$_n$ (n being an integer from 0 to 3), CHX, CX$_2$ (X being halogen, carboxyl or alkoxycarbonyl), —CH=CH—, —O—, —S—, —Se—, >N—CN, >NR$_{29}$ (R$_{29}$ being hydrogen or lower alkyl), —(CH$_2$O)—, —(CH$_2$S)—, —(CH$_3$Se)—, —CH$_2$SO)—, —(CH$_2$SO$_2$)— and —(CH$_2$CO)—; wherein substituents R$_{49}$, R$_{50}$ and R$_{51}$ are independently selected from the group consisting of hydrogen, hydroxyl, (C$_1$-C$_{20}$)alkanoyloxy, (C$_3$-C$_{20}$)alkenoyloxy, (C$_3$-C$_{20}$)alkynoyloxy and (C$_7$-C$_{11}$)aroyloxy; wherein R$_{52}$ is hydrogen or lower alkyl; wherein u is an integer from 0 to 5; wherein A$^1$ and A$^{11}$ may be the same or different and are selected from the group consisting of a bond, straight- or branched-chain alkylene, straight- or branched-chain alkynylene, straight- or branched-chain alkenylene and fluoro-substituted analogs of the foregoing, wherein A$^1$ and A$^{11}$ together have a total of from 3 to 30 carbon atoms, and Y is selected from the group consisting of —O—, —S—, —Se—, —SO—, —SO$_2$—, —CO—, —NR$_{22}$—, —SiR$_{22}$R$_{22}$—, —CR$_{22}$OR$_{22}$—, —NR$_{22}$CO—, —NR$_{22}$CS—, —CONR$_{22}$—, —CSNR$_{22}$—, —COO—, —COS—, —SCO—, —CSS—, —SCS—, —OCO— and phenylene (R$_{33}$ being hydrogen or lower alkyl); R$_{21}$ is selected from the group consisting of hydrogen, straight- or branched-chain lower alkyl, lower alkenyl or lower alkynyl, (C$_3$-C$_7$)cycloalkyl, halogeno(lower)alkyl, carboxy(lower)alkyl, (lower)alkoxycarbonyl(lower)alkyl, (C$_6$-C$_{10}$)aryl, (C$_7$-C$_{11}$)arylalkyl, di(lower)alkylamino(lower)alkyl and fluoro-substituted analogs of the foregoing, and wherein X is —CONR$_{23}$—, —CSNR$_{23}$—, —NR$_{24}$CO—, —NR$_{24}$CS—, —NR$_{24}$CONR$_{23}$13 , $$-NR_{24}-\overset{\overset{\displaystyle NR_{25}}{\|}}{C}-NR_{23}-,$$

—SO$_3$N$_{23}$—, —CSS—, —SCS—, —NR$_{23}$—, —(NO)R$_{23}$—, —(PO)R$_{23}$—, —NR$_{24}$COO—, —NR$_{24}$SO$_2$—, —S—, or —SO$_2$—, (where R$_{23}$ is selected from the group consisting of hydrogen, lower alkyl, and a species which, together with R$_{21}$, forms a saturated or unsaturated heterocyclic ring having at least one nitrogen atom and, optionally, a second heteroatom selected from the group consisting of oxygen, sulfur, silicon, selenium, nitrogen and fluoro-substituted analogs of the foregoing, and where R$_{24}$ is hydrogen or lower alkyl) wherein R$_{25}$ is hydrogen, nitrile or nitro) (XR$_{21}$ may form a tetrazole ring).

The compounds shown above may inhibit androgen and estrogen biosynthesis inter alia through inhibition of sex steroid biosynthesis enzymes, including, but not limited to 17$\beta$-hydroxysteroid dehydrogenase (17$\beta$-HSD) activity. Many of the inhibitors disclosed herein also act as sex steroid antagonists which are therefore able both to inhibit sex steroid formation and to act as antagonists to sex steroid activity by blocking sex steroid receptors. For example, preferred antiestrogens which also act as inhibitors of estrogen formation include, but are not limted to, N-butyl, N-methyl-11-(16$\alpha$-chloro-3',17'$\beta$-dihydroxy estra-1',3',5'(10')-trien-7'$\alpha$-yl) undecanamide ("EM 139"), 17$\beta$-hydroxy-17$\alpha$(12'-iodododecynyl)-$\Delta^4$-androsten-3-one ("EM 150"), N-butyl, N-methyl-11-(3'-hydroxy-16'-methylen-17'-oxoestra-1',3',5'(10')-trien-7'$\alpha$-yl) undecanamide ("EM 175"), N-butyl, N-methyl-11-(3',17'$\beta$-dihydroxy-16'-methylen estra-1',3',5'(10')-trien-7'$\alpha$-yl) undecanamide ("EM 186"), N-butyl, N-methyl-11-(3',17'$\beta$-dihydroxy-19'-nor-(17'$\alpha$) pregn-1',3',5'(10')-20'-yn-7$\alpha$-yl) undecanamide ("EM 104"). Sex steroid inhibitor progesties of the compounds of the present invention, especially the blockade of androgen and estrogen formation, may play a crucial role in the therapeutic efficacy of the compounds when administered for the treatment of estrogen- as well as androgen-sensitive diseases. Such diseases include, but are not limited to, malignant as well as non-malignant steroid-sensitive diseases, especially brease cancer, prostate cancer, ovarian cancer, endometrial cancer, endometriosis, uterine leiomyomata, precocious puberty, hirsutism, acne, seborrhea, androgenic alopecia, benign prostatic hyperplasia, sexual deviants as well as for male and female contraception. These newly discovered properties permit a blockade at a step preceeding steroid receptors, thus acting prior to and in addition to the action of steroid antagonists (e.g. antiestrogens or antiandrogens).

The invention further provides novel inhibitors of sex steroid formation. Preferred inhibitors include the compounds of general formula I set forth below. Especially preferred are those compounds of general formula I wherein $R_{16(\beta)}$ is chlorine, bromine, fluorine or iodine, or wherein $R_{14(\alpha)}$ and $R_{16(\beta)}$ togehter form $=CG_2$ (G being hydrogen, halogen lower alkyl, lower alkenyl, lower aklynyl, nitrile, alkoxycarbonyl, alkycarbonyl or carboxyl).

According to the invention, the above-indicated activities are preferably obtained inter alia with a steroid derivatives of the general formula I:

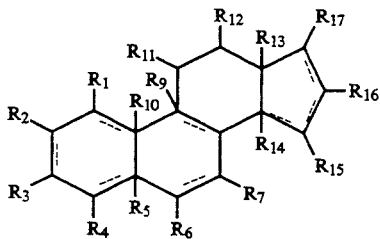

As used herein, the terms $R_1$, $R_2$, ..., $R_{17}$ refer to substituents whose locations on the steroid nucleus are illustrated in the formula I, wherein the dotted lines represent optional double bonds and wherein the A-ring is optionally aromatic. Unless specifically designated to the contrary, substituents may have either $\alpha$ or $\beta$ stereochemistry, or an R group may represent two substituents, one in an $\alpha$ position and the other in $\beta$ position.

The optional double bonds are independent from each other. In some embodiments, no double bonds are present. When appropriate, a salt of the estradiol derivatives may be used. Carbon atoms of the steroidal nucleus whose substituents are not expressly defined in a structural formula may optionally be substituted or unsubstituted. Those carbon atoms having a defined substituent may optionally be further substituted by a second substituent. As used herein, the term "lower", when describing a carbon-containing moiety, means a moiety having 8 or fewer carbon atoms. For instance, a "lower alkyl" means a $C_1$ to $C_8$ alkyl.

Certain preferred substituents of steroid derivatives in accordance with the invention include, but are not limited to, the following:

$R_1$, $R_2$ and $R_4$ are preferably independently selected from the group consisting of hydrogen, hydroxyl, halogen, lower alkyl, lower alkoxy, alkylsulfonyl lower alkoxy, arylsulfonyl lower aloxy, lower alkylsilyl, amino and nitro;

$R_3$ is preferably selected from the group consisting of hydroxyl, halogen, lower alkyl, lower alkoxy (such as methoxy, ethoxy, propoxy or hydroxyethoxy), lower alkoxy carbonyloxy, carboxy, ($C_1$-$C_{20}$)alkanoyloxy (such as acetate, propionate, butyrate, hemisuccinate, oenanthate, cypionate or cyclohexanecarboxylate), ($C_3$-$C_{20}$)alkenoyloxy, ($C_3$-$C_{20}$)alkynoyloxy, ($C_7$-$C_{10}$)aroyloxy (such as benzoate) and a divalent common species formed jointly by $R_3(\alpha)$ and $R_3(\beta)$, said divalent common species being selected from the group consisting of $=O$, $=S$, $=NR_{36}$ or $=NOR_{35}$ wherein $R_{36}$ is hydrogen or lower alkyl;

$R_5$ and $R_{10}$ are absent or preferably selected from the group consisting of hydrogen or lower alkyl;

$R_5$ is preferably selected from the group consisting of hydrogen, hydroxyl, halogen, lower alkyl, amino and nitrile;

$R_7$ is preferably in the $\alpha$ position and is preferably selected from the group consisting of hydrogen, hydroxyl, halogen, lower alkyl, lower alkoxy, lower alkylsilyl, amino, nitro, nitroso, nitrile, alkyl sulfonyl, aryl sulfonyl, lower alkylamino, diloweralkylamino, $AXR_{21}$ and $A^1$-$[Y$-$A^{11}]_u$-$X$-$R_{21}$ wherein;

A is straight- or branched-chain ($C_1$-$C_{30}$)alkylene, ($C_2$-$C_{30}$)alkenylene, ($C_2$-$C_{30}$)alkynylene, fluoro-substituted analogs of the foregoing, wherein u is an integer from 0 to 5, wherein $A^2$ and $A^{11}$ may be the same or different and are selected from the group consisting of a bond, straight- or branched-branched-chain alkylene, straight- or branched-chain alkynylene, straight- or branched-chain alkenylene, and fluoro-substituted analogs of the foregoing, wherein $A^1$ and $A^{11}$ together have a total of from 3 to 30 carbon atoms, and Y is selected from the group consisting of —O—, —S—, —Se—, —SO—, —SO$_2$—, —CO—, —NR$_{22}$—, —SiR$_{22}$R$_{22}$—, —CR$_{22}$OR$_{22}$—, —NR$_{22}$CO—, —NR$_{22}$CS—, —CONR$_{22}$—, —CSNR$_{22}$—, —COO—, —COS—, —SCO—, —CSS—, —SCS—, —OCO— and phenylene; (where $R_{22}$ is hydrogen or lower alkyl), wherein $R_{21}$ is selected from the group consisting of hydrogen, straight- or branched-chain lower alkyl, lower alkenyl or lower alkynyl, ($C_3$-$C_7$)cycloalkyl, halogeno(lower)alkyl, carboxy(lower)alkyl, (lower)alkoxycarbonyl(lower)alkyl, ($C_6$-$C_{10}$)aryl, ($C_7$-$C_{11}$)arylalkyl, di(lower)alkylamino(lower)alkyl and fluorosubstituted analogs of the foregoing, and wherein X is —CONR$_{23}$—, —CSNR$_{23}$—, —NR$_{24}$CO—, —NR$_{24}$CS—, —NR$_2$-$_4$CONR$_{23}$13 ,

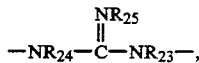

—SO$_2$NR$_{23}$—, —CSS—, —SCS—, —NR$_{23}$—, —(NO)R$_{23}$—, —(PO)R$_{23}$—, —NR$_{24}$COO—, —NR$_{24}$SO$_2$—, —S—, or —SO$_2$—, (where $R_{23}$ is selected from the group consisting of hydrogen, lower alkyl, and a species which, together with $R_{21}$, forms a saturated or unsaturated heterocyclic ring having at least one nitrogen atom and, optionally, a second heteroatom selected from the group consisting of oxygen, sulfur, silicon, selenium, nitrogen and fluoro-substituted analogs of the foregoing, and where $R_{24}$ is hydrogen or lower alkyl); wherein $R_{25}$ is hydrogen, nitrile or nitro; $XR_{21}$ may form a tetrazole ring in certain embodiments;

$R_{11}$ is preferably selected from the group consisting of hydrogen, lower alkyl, lower alkenyl, lower alkynyl, ($C_6$-$C_{10}$)aryl, alkyl sulfonyl, aryl sulfonyl, a substituted 5- or 7-member heterocyclic ring having at least one hetero atom (selected from oxygen, sulfur, silicon, selenium, nitrogen), —(CH$_2$)$_s$W (wherein W is nitrile, hydroxyl, azido, nitroso, nitro, thionitrile, halogen, alkyl sulfonyl, aryl sulfonyl and s is an integer from 1 to 6), OR$_{26}$ (wherein R$_{25}$ is hydrogen, lower alkyl or (C$_5$-C$_{10}$)aryl), DR$_{27}$ (wherein D is —Se—, —NR$_{25}$—, —S— or —O—, and R$_{27}$ is hydrogen or lower alkyl), =O, =S, =Se, =NR$_{28}$ and =NOR$_{28}$ (wherein R$_{28}$ is hydrogen or lower alkyl);

R$_{12}$ and R$_{13}$ are preferably independently hydrogen or lower alkyl;

R$_{14}$ is preferably selected from the group consisting of hydrogen, hydroxyl, nitrile, nitro, nitroso, halogen, lower alkyl, lower alkoxy, lower alkylsulfonyl, lower alkylseleno, lower alkylamino and diloweralkylamino, or R$_{14}$ and R$_{15}$ together are —CH$_2$—, —CHX—, —CX$_2$— (where X is halogen, carboxyl or alkoxycarbonyl), —O—, —S—, —Se—, >N—CN, >NR$_{29}$ or >NCOR$_{29}$ (where R$_{29}$ is hydrogen or loweralkyl);

R$_{15}$ and R$_{16}$ are preferably independently selected from the group consisting of hydrogen, hydroxyl, nitro, nitroso, halogen, lower alkyl, lower alkenyl, lower alkynyl, lower alkoxy, lower alkylseleno, lower alkylamino, di(lower)alkylamino, nitrile, azido, arylseleno, alkyl sulfonyl, aryl sulfonyl, AXR$_{21}$, A$^1$-[Y—A$^{22}$]$_u$—X—R$_{21}$, or R$_{16}$($\alpha$) and R$_{15}$($\beta$) together are =CG$_2$ (where G is hydrogen, halogen, lower alkyl, lower alkenyl, lower alkynyl, nitrole, alkoxycarbonyl, alkylcarbonyl and carboxyl), or R$_{15}$ and R$_{16}$ together are —CH$_2$—, —CHI—, —CI$_2$—, (where I is halogen, carboxyl or alkoxycarbonyl), —O—, —S—, —Se—, >N—CN, >NR$_{29}$ and >NCO$_2$R$_{29}$ (where R$_{29}$ is hydrogen or lower alkyl);

R$_{17(\alpha)}$ is preferably selected from the group consisting of hydrogen, hydroxyl, lower alkyl, halogeno(lower)alkyl, AXR$_{21}$, A$^1$-[Y—A$^{11}$]$_u$—X—R$_{21}$, B$^1$—T—R$_{30}$ (where B$^1$ is straight- or branched-chain (C$_1$-C$_{12}$)alkylene, (C$_2$-C$_{12}$)alkylene, (C$_3$-C$_{12}$)alkynylene, or (C$_2$-C$_{12}$)alkenylene, where T is —O—, —NR$_{31}$—, —Se—, —S— or S—S and R$_{30}$ and R$_{31}$ are independently hydrogen or lower alkyl, or R$_{30}$ and R$_{31}$ together are (C$_3$-C$_7$)cycloalkyl, (C$_5$-C$_7$)cycloalkenyl, (C$_3$-C$_7$)cycloalkyl or (C$_5$-C$_7$)cycloalkenyl (said cycloalkenyl having one or more hydrogen atoms replaced by halogen atoms). —HC=CHR$_{32}$ and —C≡CR$_{33}$ wherein R$_{32}$ and R$_{33}$ are independently hydrogen, halogen, tri(loweralkyl)silyl, carboxyl, carbonyl lower alkoxy, nitrile, sulfinyl lower alkyl, (C$_2$-C$_{10}$)alkyl, (C$_1$-C$_{20}$)halo alkyl, AXR$_{21}$, A$^1$-[Y—A$^{11}$]$_u$—X—R$_{21}$, a species represented by the formula

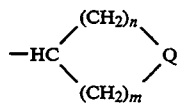   a wherein n and m are independent intergers from 0 to 6 and Q is —Se—, —SiH$_2$—, —S—, —O— or —NR$_{34}$— (wherein R$_{34}$ is hydrogen, lower alkyl or (C$_1$-C$_7$)alkanoyl), a species represented by the formula

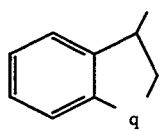   b where q is —CH$_2$—, —S—, —O— or —NR$_{35}$ (R$_{35}$ being hydrogen or lower alkyl);

R$_{17(\beta)}$ is preferably selected from the group consisting of hydrogen, hydroxyl, halogen, 1-oxo-2-propynyl, 1-hydroxy-2-propynyl, (C$_1$-C$_7$)alkanoyloxy (such as acetate, propionate, butyrate, hemisuccinate, oenanthate, cypionate or cyclohexanecarboxylate, (C$_3$-C$_7$)alkenoyloxy, (C$_3$-C$_7$)alkynoyloxy, alkylcarbonyl, alkenyloxy, cycloalkenyloxy, 1-alkyloxy-alkyloxy, 1-alkyloxy cycloalkyloxy, alkylsilyloxy and a divalent common species formed jointly by R$_{17(\alpha)}$ and R$_{17(\beta)}$, said divalent common species being selected from the group consisting of =O, =S, =NR$_{36}$ or =NOR$_{36}$ wherein R$_{36}$ is hydrogen or lower alkyl.

In certain preferred embodiments, R$_{17(\alpha)}$ is hydroxyl. In other preferred embodiments, at least one substituent selected from the group consisting of R$_{7(\alpha)}$, R$_{15}$, R$_{16}$ and R$_{17(\alpha)}$ is A$^1$-[Y—A$^{11}$]$_u$—X—R$_{21}$.

A useful non-steroidal inhibitor has general formula IV:

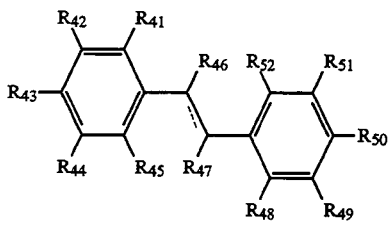   IV where the dotted lines represent an optional double bond of Z or E configuration.

Certain preferred substituents include, but are not limited to the following:

R$_{41}$, R$_{45}$, R$_{48}$, R$_{52}$ are preferably independently selected from the group consisting of hydrogen, hydroxyl, halogen, lower alkyl, lower alkoxy, alkylsulfonyl lower alkoxy, arylsulfonyl lower alkoxy, lower alkylsilyl, amino, nitro, nitrile and nitroso.

R$_{43}$, R$_{44}$, R$_{49}$ and R$_{51}$ are preferably independently selected from the group consisting of hydrogen, hydroxyl, halogen, lower alkyl, lower alkoxy, alkylsulfonyl lower alkoxy, arylsulfonyl lower alkoxy, lower alkylsilyl, amino, nitrile, nitro, nitroso, azido, lower alkylamino, dilower alkylamino, AXR$_{21}$, Y$_{47}$-A$^1$[Y—A$^{11}$]$_u$—X—R$_{21}$, and A$^1$-[Y—A$^{11}$]$_u$—X—R$_{21}$ wherein A, A$^1$, A$^{11}$, X, Y and u are defined as previously in formula I and wherein Y$_{47}$ is absent or selected from the group consisting of carbonyl and carboxyl.

R$_{43}$ and R$_{50}$ are preferably independently selected from the group consisting of hydrogen, hydroxyl, halogen, lower alkyl, lower alkoxy (such as methoxy, ethoxy, propoxy or hydroxyethoxy), lower alkoxy carbonyloxy, carboxyl, (C$_1$-C$_{20}$) alkanoyloxy (such as acetate, propionate, butyrate, hemisuccinate, oenanthate, cypionate or cyclohexanecarboxylate), (C$_3$-C$_{20}$) alkenoyloxy, (C$_3$-C$_{20}$) alkynoyloxy, (C$_7$-C$_{11}$) aroyloxy and alkylsilyloxy.

R$_{46}$ and R$_{47}$ are preferably independently selected from the group consisting of hydrogen, amino, lower alkylamino, dilower alkyl amino, nitro, nitrile, nitroso, halogen, lower alkyl, lower alkenyl, lower alkynyl, halogeno lower alkyl, helogeno lower alkenyl, halogeno lower alkynyl, alkyl sulfonyl, aryl sulfonyl, a substituted 5- to 7-member heterocyclic ring having at least one heteroatom (selected from oxygen, sulfur, silicon, selenium, nitrogen), —(CH$_2$)$_s$V (wherein V is nitrile, hydroxyl, azido, nitroso, alkoxy, nitro, thionitrile, halogen, alkyl sulfonyl or aryl sulfonyl and s is an integer from 1 to 6), a moiety of the formula:

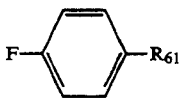 c wherein:
F is absent or selected from the group consisting of alkyl, carbonyl, or carboxyl, wherein the phenyl ring may be halogenated, wherein $R_{61}$ is hydrogen, hydroxyl, halogen, lower alkyl, lower alkenyl, lower alkynyl, nitrile, nitro, nitroso or $X_{45}(CH_2)_nY_{45}$ ($X_{46}$ being selected from the group consisting of —O—, —S—, —Se—, —SO—, —SO$_2$— and —CO—, and $Y_{45}$ being selected from the group consisting of hydroxyl, amino, monoalkyl amino, dialkyl amino, dimethyl N-oxide, N-aziridyl, guanidino, N-pyrrolidino, N-piperidino, N-methylpiperazino, N-morpholino and alkoxy, and n being an integer from 1 to 6, preferably 3); $AXR_{21}$, $Y_7$-$A^1$-$[Y$-$A^{11}]_u$-$X$-$R_{21}$, and $A^1$-$[Y$-$A^{11}]_u$-$X$-$R_{21}$, wherein, A, $A^1$, $A^{11}$, X, Y, $Y_{37}$ and u are defined as previously for $R_{42}$, $R_{44}$, $R_{49}$ and $R_{51}$.

$R_{45}$ and $R_{47}$ may also be a species which, in combination with another substituent of general molecular formula III, form a moiety selected from the group consisting of: —CH$_2$—, CHX, CX$_2$ (X being halogen, carboxyl or alkoxycarbonyl), —O—, —S—, —Se—, >N—CN, >NR$_{29}$ and >NCO$_2$R$_{29}$ (R$_{29}$ being hydrogen or lower alkyl), lower alkylene, —CH(CH$_3$)—, —CH=CH—, —(CH$_2$)$_r$O(CH$_2$)$_s$—, —(CH$_2$)$_r$S(CH$_2$)$_s$—, —(CH$_2$)$_r$Se(CH$_2$)$_s$—, —(CH$_2$)$_r$SO(CH$_2$)$_s$—, —(CH$_2$)$_r$SO$_2$(CH$_2$)$_s$—, —(CH$_2$)$_r$CO(CH$_2$)$_s$—, —(CH$_2$)$_r$NR$_{22}$(CH$_2$)$_s$—, —(CH$_2$)$_r$SiR$_{22}$R$_{22}$(CH$_2$)$_s$— or —(CH$_2$)$_r$CR$_{22}$OR$_{22}$(CH$_2$)$_s$— (wherein R$_{22}$ being hydrogen or lower alkyl, r and s being independent integers from 0 to 3), a moiety of the formula:

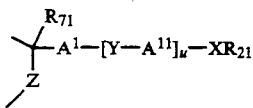 d wherein:
$A^1$, Y, $A^{11}$, u, X and $R_{21}$ are as defined above, wherein Z is absent or is selected from the group consisting of lower alkylene, halogeno lower alkylene, —(CH$_2$)$_n$O—, —(CH$_2$)$_n$S—, —(CH$_2$)$_n$Se—, —(CH$_2$)$_n$SO—, —(CH$_2$)$_n$SO$_2$—, —(CH$_2$)$_n$CO—, —(CH$_2$)$_n$NR$_{33}$—, —(CH$_2$)$_n$ SiR$_{22}$R$_{22}$— and —(CH$_2$)$_n$CR$_{22}$OR$_{22}$—, R$_{22}$ as defined above, n being an integer from 0 to 3, and $R_{71}$ being selected from a group consisting of hydrogen, hydroxyl, halogen, lower alkyl, lower alkoxy and lower alkylsilyl, a moiety of the formula:

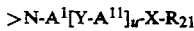 8 wherein N is nitrogen atom and $A^1$, $A^{11}$, u, Y, X and $R_{21}$ are as defined above.

In preferred embodiments, moieties which are combinations of R groups from general molecular structure IV, are combinations of $R_{46}$ and $R_{47}$, $R_{46}$ with $R_{41}$ or $R_{52}$, or $R_{47}$ with $R_{45}$ or $R_{48}$.

The foregoing compounds are potent inhibitors of sex steriod formation, especially 17$\beta$-hydroxysteroid dehydrogenase activity. This may be demonstrated by inhibiting enzymatic activity in vitro using purified enzyme from human placenta (Thomas et al., J. Biol. Chem. 258, 11500–11504, 1983). The antiestrogenic activity of the compounds is measured in vitro in estrogen-sensitive human breast cancer cells ZR-75-1 (Poulin et al., Cancer Res. 46, 4933–4937, 1986) while the in vivo action is measured as the potency of the compound to reverse the estradiol-induced increase of uterine weight in adult ovariectomized mice.

In particular, a preferred inhibitor produces antisteroid effects at a dose possessing no agonistic activity, unlike compounds such as Tamoxifen, which possesses some agonistic properties which limit their therapeutical efficiency (Wakeling and Bowler, J. Steroid Biochem. 30, 141–147, 1988).

Such compounds administered at appropriate doses are of value in all conditions where antiestrogens and antiandrogens are beneficial. In particular, this approach is of value in breast cancer, prostate cancer, endometrial cancer, ovarian cancer, endometriosis, benign prostatic hyperplasia, precocious puberty, hirsutism, acne, seborrhea, androgenic alopecia, menstrual disorders and as male and female contraceptive as well as in sexual deviants.

When used to block 17$\beta$-hydroxysteroid dehydrogenase activity, and for antiandrogenic and antiestrogenic effects in warm-blooded animals, a typical daily dose is 0.1 to 25 mg/kg administered by injection or orally. In man, this is equivalent to an oral dose of 2.5 to 1250 mg/day. The compounds are more conveniently administered to main in the form of a pharmaceutical composition.

When patients whose tests or ovaries, respectively, have already been surgically removed are treated according to this invention, the administration and dosage of the above-described compound (multi sex hormone blocker) are the same as in intact patients or patients receiving an LHRH agonist or antagonist.

The hormone blocker useful in the present invention is typically compounded in customary ways for oral administration, e.g., in capsules, tablets, as dragees or even in liquid form, e.g., suspensions or syrups. The active substance, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycols. Of course, tase-improving substances can be added in the case of oral administration forms.

The therapeutically active hormone blocker should be present in a concentration of about 0.5–90% by weight of the total mixture, i.e., in amounts that are sufficient for maintaining the above-mentioned dosage range.

As further forms of administration, one can use plug capsules, e.g., of hard gelatin, as well as closed soft-gelatin capsules comprising a softener or plasticizer, e.g., glycerine. The plug capsules contain the active substance preferably in the form of a granulate, e.g., in mixture with fillers, such as lactose, saccharose, mannitol, starches, such as potato starch or amylopectin, cellulose derivatives or highly-dispersed silica acids. In soft-gelatin capsules, the active substance is preferably dissolved or suspended in liquids, such as vegetable oils or liquid polyethylene glycols.

In place of oral administration, all the active compounds may be administered parentally. In such case, one can use a solution of the active substance, e.g., in sesame oil or olive oil.

The hormone blocker may also be microencapsulated in or attached to a biocompatable, biodegradable polymer, e.g., poly(d,l-lactide-coglycolide) and subcutaneously or intramuscularly injected by a technique called subcutaneous or intramuscular depot to provide continuous, slow release of the compound over a period of 15 days or longer.

The composition may contain, in addition to the storoid and/or nonsteroidal derivatives of the invention, other antiestrogens and/or antiandrogens and/or enzymatic inhibitors and/or inhibitors of ACTH and/or growth hormone and/or prolactin secretion.

Set forth below, by way of example and not by way of limitation, are some preferred techniques for synthesis of preferred inhibitors of sex steroid formation in accordance with the invention. Those of skill in the art will recognize conventional variations for producing modifications or analogs of the various compounds shown in the synthetic pathways described below.

SYNTHESIS OF PREFERRED INHIBITORS

Instrumentation

IR spectra were obtained in a Perkin-Elmer spectrometer 1310. UV spectra were recorded in methanol on a Beckman DU-6 spectrometer. H-NMR spectra were obtained at 200 MHz on a Varian XL-200 spectrometer. Chemical shifts are reported in ppm units with tetramethylsilane as internal standard. Mass spectra were obtained on Micromass 16F spectrometer.

EXAMPLE 1

Synthesis of the N-butyl, N-methyl-11-(3′,17′β-dihydroxy-16′-methylenestar-1′,3′,5′(10′)-trien-7′-α-yl) undecanamide ("EM 186") (The synthesis of this compound is described in the scheme I where n=10)

N-butyl, N-methyl-11-(3′-hydroxy-16′-methylen-17′-oxo-estra-1′,3′,5′(10′) trien-7′α-yl) undecanamide ("EM 175")

A mixture of N-butyl, N-methyl-11-(3′,17′β-dihydroxy-estra-1′,3′,5′-(10′)-trien-7α-yl) undecanamide (1) (427 mg, 1 mM), paraformaldehyde (150 mg, 5 mM), dry dimethylamine hydrochloride (466 mg, 7 mM) isoamyl alcohol (10 ml) is refluxed for 2 hours. After concentration under reduced pressure, the reaction mixture is poured in dilute hydrochloric acid (1:9, 50 cc), washed with ether (X3), alkalinized by adding a saturated solution of sodium carbonate and extracted (3X) with chloroform. The chloroform layers are washed with water and concentrated to dryness. Water is added to the resulting oil and the mixture is subjected to steam distillation until the distillate is neutral. The residue is cooled and subjected to "flash chromatography" on silica gel (Kieselgel 60, Merck, 250 mesh ASTM). The elution performed with a mixture of hexane, ethyl acetate (7:3 v/v) gives the N-butyl, N-methyl-11-(3′-hydroxy-16′-methylen-17′-oxo-estra-1′,3′,5′(10′)-trien-7′α-yl) undecanamide ("EM 175").

N-butyl, N-methyl-11-(3′,17′β-dihydroxy-16′-methylen-estra-1′,3′,5′(10′)-trien-7′α-yl) undecanemaide ("EM 186")

N-butyl, N-methyl-11-(3′-hydroxy-16′-methylen-17′-oxo-estra-1′,3′,5′(10′)-trien-7′α-yl) undecaneamide ("EM 175") (400 mg) obtained above is dissolved in 10 ml of methanol and mixed with a solution of 200 mg of sodium borohydride in 10 ml of water. After stirring for three hours at room temperature, a drop of acetic acid is added. The mixture poured in saturated sodium chloride solution is extracted with ethyl acetate (3X). The organic layers are washed with water, dried on anhydrous MgSO4 and evaporated to dryness under reduced pressure. The residue is chromatographed on silica gel (Kieselgel, 60F254, Merck, 0.063, 0.200 mm, 20 g). Elution with a mixture of hexane-ethyl acetate (6:4 v/v) gives the N-butyl, N-methyl-11-(3′,17′β-dihydroxy-16′-methylen-estra-1′,3′,5′(10′)-trien-7α-yl) undecaneamide ("EM 186").

3′-benzoate of N-butyl, N-methyl-11-(3′,17′β-dihydroxy-16′-methylen-estra-1′,3′,5′(10′)-trien-7α-yl) undecanemaide The 16-methylen-3,17β-alcohol ("EM 186") (45 mg, 0.1 mmol) obtained previously is dissolved in acetone (1 ml) and a sodium hydroxide solution (1N, 120 μl). The mixture is cooled to 0° C. and benzoyl chloride (14 μl, 0.12 mmol) is added dropwise. The mixture is then stirred for 40 minutes at 0° C. and then diluted with water. The solution is extracted with ethyl acetate (3X) and the organic layers are washed with a saturated sodium bicarbonate solution and water. The ethyl acetate solution is dried under vacuum. The residue is immediately chromatographed on silica gel (Kieselgel, 60F254, 0.063–0.200 mm, 500 g). Elution with hexane ethyl acetate (4:1 v/v) give the 3-benzoate of N-butyl, N-methyl-11-(3′,17′β-dihydroxy-16′-methylen-estra-1′,3′,5′(10′)-trien-7′α-yl) undecaneamide.

By methods analogous to those described above and using the same or other corresponding starting materials and the same or corresponding acid chloride, the following synthesis are performed. One can thus prepare esters or other corresponding 2 to 20 carbon hydrocarbon carboxylic acid esters of N,N′ dialkyl-11-(3′,17′β-dihydroxy-16′-methylen-estra-1′,3′,5′(10′)-trien-7α-yl) alkamides 2 as summarized in Table 1.

TABLE 1

N,N′ dialkyl-11-(3′,17′β-dihydroxy-16′-methylen-estra-1′,3′,5′(10′)-trien-7′α-yl) alkylamide

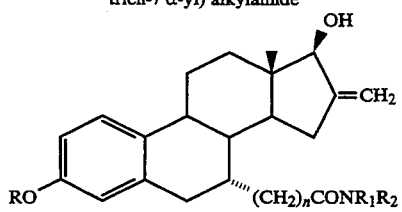

| n | R | R₁ | R₃ |
|---|---|----|----|
| 10 | H | methyl | n-butyl |
| 10 | H | H | n-butyl |
| 10 | H | methyl | 1H, 1H-heptafluorobutyl |
| 10 | H | methyl | n-pentyl |
| 10 | C₆H₅CO | methyl | n-butyl |
| 10 | CH₃CO | methyl | n-butyl |
| 10 | C₃H₅CO | methyl | n-butyl |
| 10 | C₆H₂₃CO | methyl | n-butyl |
| 10 | Cyclo C₅H₉—(CH₃)CO | methyl | n-butyl |
| 10 | C₆H₁₁CO | methyl | n-butyl |
| 10 | CH₃(CH₂)₁₆CO | methyl | n-butyl |
| 9 | H | methyl | n-butyl |

TABLE 1-continued

N,N' dialkyl-11-(3',17'β-dihydroxy-16'-methylen-estra-1',3',5'(10')-trien-7'α-yl) alkylamide

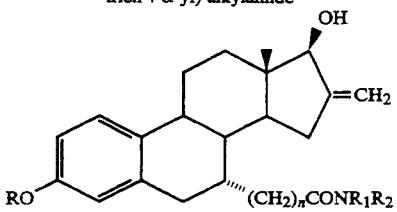

| n | R | R₁ | R₃ |
|---|---|---|---|
| 9 | C₆H₅CO | methyl | n-butyl |
| 9 | C₃H₇CO | methyl | n-butyl |
| 8 | H | methyl | n-butyl |
| 8 | C₆H₃CO | methyl | n-butyl |

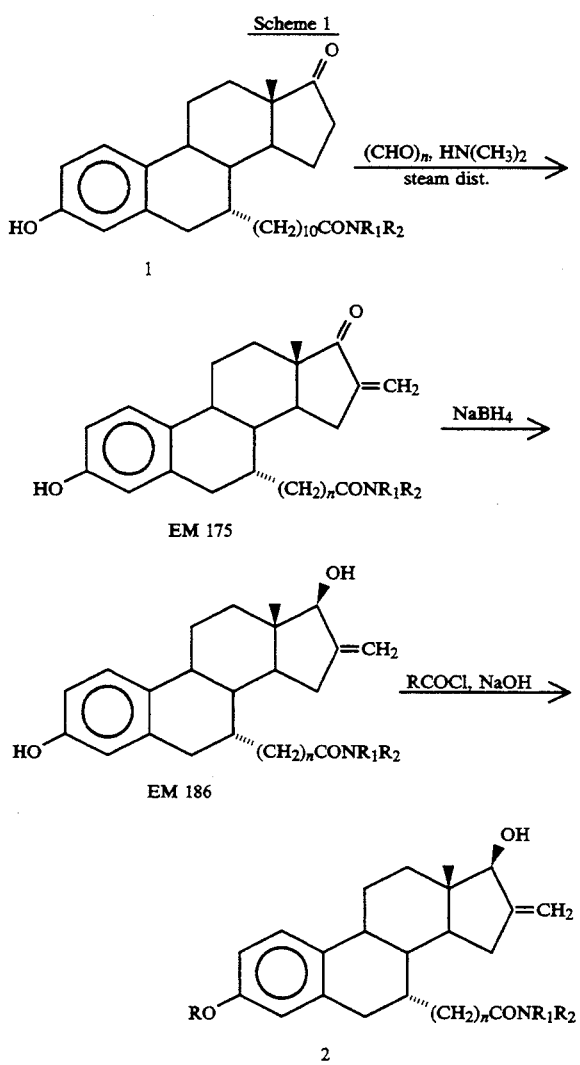

Scheme 1

EXAMPLE 2

Synthesis of N-butyl, N-methyl-11-(16α-chloro-3',17'β-dihydroxy-estra-1',3',5'(10')-trien-7'α-yl) undecanamide ("EM 139", Scheme 2)

N-butyl, N-methyl-11-(3',17'-diacetoxy-estra-1',3',5'(10'), 16'-tetraen-7'α-yl) undecanamide (5)

To 11-(3-benzoyloxy-17-oxo-estra-1,3,5(10)-trien-7α-yl) undecanoic acid (3) (3.94 g, 7.22 mmol) (prepared as described in Bucourt et al., J. Biol. Chem. 253: 8221–8228, 1978, which is hereby incorporated herein by reference), dissolved in anhydrous $CH_2Cl_3$ (100 ml) and cooled at −10° C. was added tributylamine (2.18 ml, 9.15 mmol) and isobutylchloroformate (1.30 ml. 10.0 mmol). The solution was stirred during 35 min. and N-methylbutylamine (13 ml, 109.7 mmol) was added. The mixture was warmed to room temperature and stirred during 1 h. Afterward, $CH_2Cl_2$ was added and the organic phase was washed with 1N HCl, water saturated sodium bicarbonate solution and finally with water, dried with anhydrous $MgSO_4$ and the solvent was removed under reduced pressure. The residue was purified by chromatography on silica gel. Elution with mixture of EtOAc/hexane (1.5:8.5 v/v) yielded N-butyl, N-methyl-11-(3'-benzoyloxy-17'-oxo-estra-1',3'5'(10')-trien-7'α-yl) undecanamide (4.25 g, 96%) as colorless oil; IR $\nu$ (neat) 1750, 1725 and 1640 cm$^{-1}$. The above described benzoyloxy amide (341 mg, 0.54 mmol) was dissolved in methanol (10 ml) and cooled at 0° C. Following this 2N NaOH (5 ml) was added and the mixture was stirred during 60 min. at 0° C. The solution was neutralized with 1N HCl and extracted with $CH_2Cl_2$. The organic phase was dried with anhydrous $MgSO_4$ and the solvent was removed under reduced pressure. The residue was purified by chromatography on silica gel. Elution with mixture of EtOAc/hexane (3:7 v/v) yielded N-butyl, N-methyl-11-(3'-hydroxy-17'-oxo-estra-1',3',4'(10')-trien-7'α-yl) undecanamide (4) 284 mg, 97%) as colorless oil; $^1$H-NMR $\delta$ (CDCl₃) 0.91 (s, 3H,18'-CH₂), 2.76$_{app}$ (d,1HJ=16.3 Hz, part of ABX system 6'-H) 2.96 and 2.98 (2s,3H N-CH₃), 3.27 and 3.38 (2t$_{app}$,2H,J=7.5 Hz,N-CH₂—), 6.63 (broad s,1H,4'-H), 6.70 (broad d,1H,J=8.5 Hz,2'-H), 7.12 (d,1H,J=8.4 Hz,1'-H); IR $\nu$ (neat) 3270, 1730, 1615 cm$^{-1}$; MS m/e 523 (M+,100%), 508 (M+-CH₃,32%, 142 (C₂H₄CON(CH₃)C₄H₉+, 47%). The ketone amide 4 (163 mg, 0.50 mmol) was dissolved in isoprenyl acetate (10 ml). p-Toluenesulfonic acid (44 mg) was then added and the solution was distilled to about two-thirds of the original volume in 7 hrs and was then stirred at reflux for 12 hrs. Afterwards, the solution was cooled with an ice-water bath and extracted with 50 ml of cooled ether. The ether was washed with a cooled satured sodium bicarbonate and water. The organic phase was dried with anhydrous $MgSO_4$ and the solvent was removed under reduced pressure. The residue was filtered through alumina (15 mm×50 mm, alumina Woehlm neutral, activity II) using a mixture of benzene-diethyl ether (3:7 v/v) as eluant. The solvent was removed under reduced pressure and, the residue was purified by flash chromatography on silica gel. Elution with mixture of EtOAc/hexane (1:4 v/v) yielded the N-butyl, N-methyl-11-(3',17'-diacetoxy-estra-1',3',5'(10'), 16'-tetraen-7'α-yl) undecanamide (5) (244 mg, 80%) as colorless oil; $^1$H-NMR $\delta$ (CDCl₃) 0.92 (s,3H,18'-CH₃), 0.92 and 0.95 (2t,3H,J=7.0 Hz,N(CH₂)₃CH₃), 2.18 (s,3H,17'-OCOCH₃), 2.28(s,3H,3'-OCOCH₃), 2.76 app (d,1H,J=16.1 Hz, part of ABX system, 6'-H, 2.90 and 2.96 (2s,3H,N-CH₃), 3.26 and 3.35 (2t$_{app}$,2H,J=7.6 Hz,N-CH₂—), 5.52 (m,1H,16'-H), 6.80 (broad s,1H,4'-H), 6.85 (dd,1H,J₁=9.1 Hz and J₂=3.0 Hz,2'-H), 7.27 (d,1H,J=9.1 Hz,1'-H); IR $\nu$ (neat) 1750, 1635, 1200 cm$^{-1}$; MS m/e 607 (M+,2%), 565 (M+-COCH₂,100%), 550 (M+-COCH₂-CH₃,13%), 523 (M+-2COCH₃,45%), 142 (C₂H₄CON(CH₃)C₄H₉+,55%), 129

($C_4H_9(CH_3)NCOCH_3^+$,38%), 114 ($C_4H_9(CH_3)NCO^+$,60%), 86 ($C_4H_9(CH_3)N^+$,25%); EXACT MASS calcd for $C_{39}H_{57}O_5N$ 607.4239, found 607.4234.

N-butyl, N-methyl-11-(16′α-chloro-3′acetoxy-17′-oxo-estra-1′,3′,5′(10′)-trien-7′α-yl) undecanamide (6)

To diacetate amide 5, dissolved in 5 ml of acetone, was added a solution of sodium acetate (2.6 equivalents) in acetic acid and water (1:11.3 v/v) and then, was treated with tertbutyl hypochlorite (1 eq.) prepared from t-butanol (4 ml) and Javel water (Javex 6.1%, 50 ml). The clear solution was warmed to 55° C. and stirred for 1 h. Afterwards, the solvent was evaporated to dryness. The residue was dissolved in ether (100 ml) and water was added (20 ml). The organic phase was washed with water, dried with anhydrous $MgSO_4$ and evaporated to dryness. The residue was purified by chromatography on silica gel carried out with mixture of EtOAc/hexane (3:7 v/v) to give the N-butyl, N-methyl-11-(16′α-chloro-3′acetoxy-17′-oxo-estra-1′,3′,4′(10′)-trien-7′α-yl) undecanamide (6) (115 mg, 89%) as colorless oil; $^1$H-NMR δ ($CDCl_3$) 0.92 and 0.95 (2t,3H,J=7.0 Hz,N($CH_2$)$_3CH_3$), 0.96 (s,3H,18′-$CH_3$), 2.28 (s,3H,3′-$OCOCH_3$), 2.80 app (d,1H,J=16.6 Hz, part of ABX system, 6′-H) 2.90 and 2.96 (2s,3H,N-$CH_3$), 3.24 and 3.35 (2t$_{app}$,2H,J=7.4 Hz,-N-$CH_2$—), 4.46 (d,1H,J=6.6 Hz,16′β-H), 6.82 (broad s,1H,4′-H), 6.86 (dd,1H,J=9.1 Hz and $J_2$=2.6 Hz,2′-H), 7.29 (d,1H,J=9.1 Hz,1′-H); IR ν (neat) 1750, 1640, 1250 cm$^{-1}$; MS m/e 601, 599 (M$^+$,24%, 68%), 142 ($C_2H_4CON(CH_3)C_4H_9^+$, 100%), 114 ($C_4H_9(CH_3)NCO^+$,93%).

N-butyl, N-methyl-11-(16α-chloro-3′,17′β-dihydroxy-estra-1′,3′,5′(10′)-trien-7′α-yl) undecanamide ("EM 139")

A stirred solution of haloketone amide 6 in anhydrous tetrahydrofuran (THF) (10 ml) under argon was chilled to −70° C. with 2-propanol/dry ice bath. A solution of 1.0M of lithium aluminium hybride (2 eq.) was then added dropwise. After 30 min, the reaction was allowed to return slowly at 0° C. for 5 min, then was quenched by the dropwise addition of a mixture of THF-EtOAc (5 ml) (1:1 v/v) and acidified at pH~4 with (10%) HCl. The mixture was stirring for 5 min. at room temperature and then extracted with EtOAc. The organic phase was washed with water, dried on anhydrous $Na_2SO_4$ and evaporated under reduced pressure. The residue included two important antiestrogens which were separated by chromatography on silica gel and eluted with a mixture of EtOAc/hexane (4:6 v/v) to give: N-butyl, N-methyl-11-(16′α-chloro-3′17′α-dihydroxy-estra-1′,3′,5′(10′)-trien-7′α-yl) undecanamide ("EM 170") (15 mg, 29%) as colorless oil; analytical sample was obtained by HPLC purification; $^1$H-NMR δ ($CDCl_3$, 400 MHz) 0.79 (s,3H,18′-$CH_3$), 0.93 and 0.96 (2t, 3H,J=7.3 Hz,N($CH_2$)$_3CH_3$), 2.80 (2H,$J_{6,6}$=17.1 Hz and $J_{6,7}$=4.5 Hz, Δδ=24.34 (Hz, system ABX, 6′-H), 2.94 and 2.99 (2s, 3H,N-$CH_3$), 3.26 (dd,$J_1$=7.6 Hz and $J_2$=7.4 Hz) and 3.32–3.43 (m)-[2H,-N-$CH_2$-], 3.71 (d,1H,J=4.5 Hz,17′β-H), 4.63 (ddd, 1H, $J_{16,15}$=10.2 Hz, $J_{16,17}$=4.5 Hz and $J_{16,15}$ 3.9 Hz, 16′β-H), 6.50 (d, 1H, J=24 Hz, 3′-OH), 6.60 (d, 1H,J=2.5 Hz, 4′-H), 6.66 (dd,1H,$J_1$=8.4 Hz and $J_3$=2.5 Hz, 2′-H), 7.14 (d,1H,J=8.5 Hz, 1′-H); IR ν (neat) 3300, 1615, 1495 cm$^{-1}$; MS m/e 561,559 (M$^+$, 40%, 100%), 523 (M$^+$-HCl, 20%), 142 ($C_2H_4CON(CH_3)C_4H_9^+$, 44%), 114 ($C_4H_9(CH_3)CNO^+$, 37%); Exact mass calculated for $C_{34}H_{54}O_3N^{35}Cl$ 559.3785, found 559.3821; and -N-butyl, N-methyl-11-(16′α-chloro 3′,17′β-dihydroxy-estra-1′3′,5′(10′)-trien-7′α-yl) undecanamide ("EM 139") (25 mg, 55%) as a colorless oil; analytical sample was obtained by HPLC purification; 1H-NMR δ ($CDCl_3$, 400 MHz), 0.81 (s,3H, 18′-$CH_3$), 0.93 and 0.96 (2t, 3H,J=7.3 Hz, ($CH_2$)$_3CH_3$), 2.78 (2H, $J_{6,6}$=16.2 Hz and $J_{6,7}$=4.5 Hz, Δ$^5$24.34 Hz, system ABX, 6′-H), 2.94 and 2.99 (2S, 3H,N-$CH_3$), 3.27 (dd, $J_1$=7.6 Hz and $J_2$=7.5 Hz) and 3.31–3.45 (M) [2H, —N—$CH_2$—], 3.86 (dd, 1H, $J_{17,17\text{-}OH}$=3.4 Hz and $J_{17,16}$=5.9 Hz, 17′α-H), 4.11 (ddd, 1H, $J_{16,15}$=10.8 Hz, $J_{16,17}$=5.9 Hz and $J_{16,15}$=2.5 Hz, 16′β-H), 6.56 (d, 1H, J=19.7 Hz, 3′-OH), 6.61 (d, 1H, J=2.5 Hz, 4′-H), 6.66 (dd, 1H, $J_1$=8.4 Hz and $J_2$=2.6 Hz, 2′-H), 7.13 (d, 1H, J=8.4 Hz, 1′-H); IR ν (neat) 3320, 1615, 1490 cm$^{-1}$; MS m/e 551,559 (M$^+$, 38%, 100%), 523 (M$^+$-HCl, 16%), 142 ($C_2H_4CON(CH_3)C_4H_9^+$, 80%), 114 ($C_4H_9(CH_3)NCO^+$,76%); Exact mass calculated for $C_{34}H_{54}O_3N^{35}Cl$ 559.3785, found 559.3825.

Scheme 2

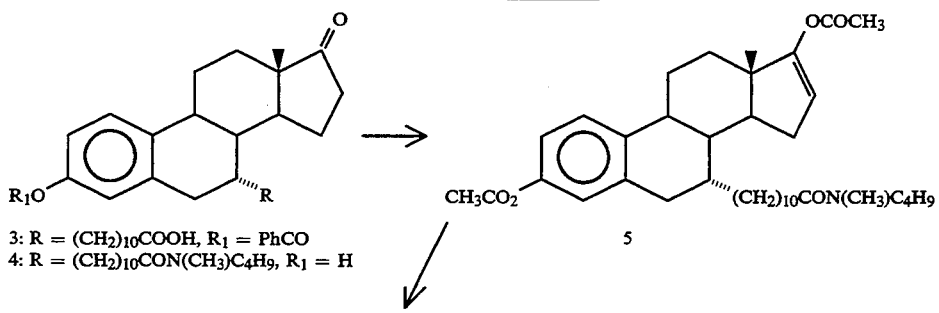

3: R = ($CH_2$)$_{10}$COOH, $R_1$ = PhCO
4: R = ($CH_2$)$_{10}$CON($CH_3$)$C_4H_9$, $R_1$ = H

-continued
Scheme 2

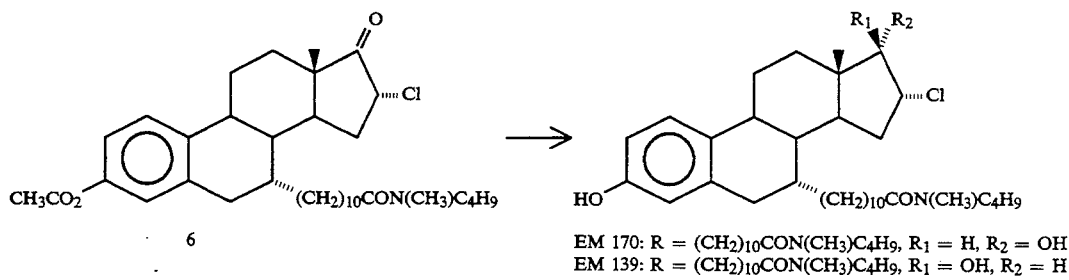

EM 170: R = (CH$_2$)$_{10}$CON(CH$_3$)C$_4$H$_9$, R$_1$ = H, R$_2$ = OH
EM 139: R = (CH$_2$)$_{10}$CON(CH$_3$)C$_4$H$_9$, R$_1$ = OH, R$_2$ = H

EXAMPLE 3

Synthesis of 17β-hydroxy-17α-(12'-iodododecynyl)-Δ$^4$-androsten-3-one ("EM 150") (Scheme 3)

3,3-ethylenedioxy-17α-ethynyl-Δ$^5$-androsten-17β-ol (8)

A mixture of ethisterone (7) (9.5 g, 30.4 mmol), ethylene glycol (3.34 g, 3 ml, 53.8 mmol) and p-toluenesulfonic acid (50 mg, 0.29 mmol) dissolved in 500 ml of dry benzene was refluxed (Dean-Stark) for 24 h under nitrogen. Then a mixture of ether and dichloromethane (1:1, 1) was added and the resulting solution washed successively with sodium carbonate (2×100 ml, 5% aqueous) and with water (4×200 ml). The organic phase was dried, filtered and concentrated to a solid. The residue (9.73 g, 90% of crude dioxolane) was used without any further purification in the next step.

(±)3,3-ethylenedioxy-17β-tetrahydropyranyloxy-17α-ethynyl-66$^5$androstene (9)

A mixture of crude dioxolane (9.73 g, 27.3 mmol) in dry dichloromethane (500 ml), 2,3-dihydropyran (6.9 g, 7.5 ml, 82.2 mmol), and catalytic pyridinium p-toluenesulfonate (100 mg, 0.4 mmol) was stirred at room temperature for 36 h. Then, ether (500 ml) was added and the resulting solution was washed successively with sodium carbonate (2×100 ml, 5% aqueous) and with water (4×200 ml). The organic phase was dried, filtered and evaporated to give 12.74 g of crude material. The residue was purified by flash chromatography (hexane:acetone, 95:5) to give 7.7 g, 58% of compound 9 along with 2.94 g, 24% of corresponding enone.

(±)3,3-ethylenedioxy-17β-tetrahydropyranyloxy-17α-(12'-iodododecynyl) Δ$^5$-androstene (10)

To a solution of butyllithium (2.84 ml of a 1.6M solution in hexane, 4.5 mmol) in dry tetrahydrofuran (THF, 45 ml) was added dropwise a solution of acetylene 9 (500 mg, 1.13 mmol) in dry THF (10 ml) at −40° C. The reaction mixture was then allowed to warm up to −10° C. and stirred for 1 h. At this temperature, a solution of 1,10-diiododecan (2.15 g, 5.4 mmol) in dry THF (5 ml) was added in one portion. The cooling bath was removed and the reaction mixture was stirred at room temperature for 15 h. Then, the solution was diluted with 100 ml of ether and was washed with water (6×30 ml), dried, filtered and concentrated to an oil. The residue was purified by flash chromatography (hexane:acetone, 96:4), followed by preparative thin-layer chromatography (TLC) to give 208 mg, 26% of compound 10 (n=10)

17β-hydroxy-17α-(12'-iodododecynyl)-Δ$^4$-androsten-3-one ("EM 150")

To a solution of the oily tetrahydropyranyl ethers (100 mg, 1.4×10$^{-4}$ mol) in ethanol (5 ml) was added aqueous oxalic acid (2 ml, 2% aqueous). The reaction mixture was heated at reflux for 2.5 h. Then, most of the ethanol was evaporated and the residue transferred into a separatory funnel with ether (40 ml) and water (20 ml) was washed thoroughly with water. The ethereal phase was dried, filtered and concentrated to an oil. The residue was purified by column chromatography (toluene:acetone, 96.4) to give 63 mg, 77% of iodoenone "EM 150".

Scheme 3

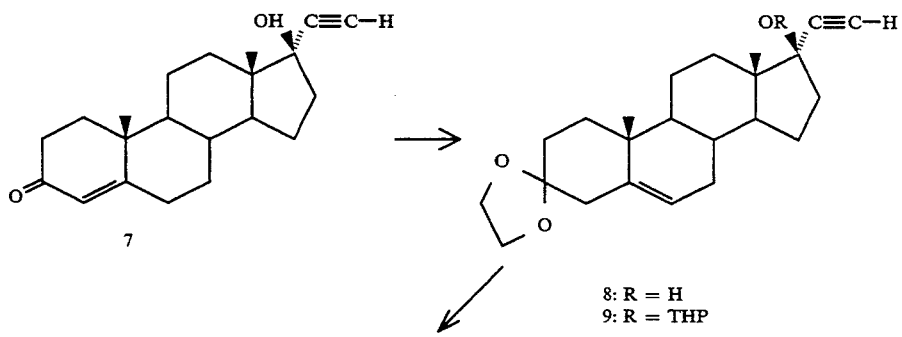

8: R = H
9: R = THP

Scheme 3 (continued)

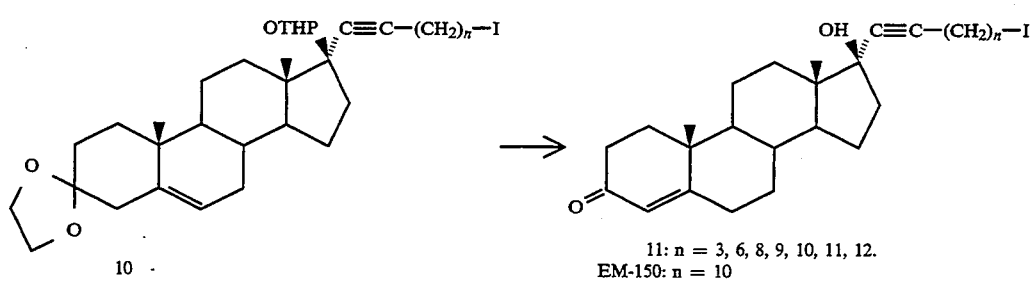

10

11: n = 3, 6, 8, 9, 10, 11, 12.
EM-150: n = 10

EXAMPLE 4

N-butyl, N-methyl-12,13-Bis-(4-hydroxyphenyl)-12-pentadecenoic amide ("EM 142", compound 16 with x=10) (Scheme 4)

This synthesis was done as described by Edwards et al. (1988) U.S. Pat. No. 4,760,061.

12,13-Bis-(4-methoxyphenyl)-11-pentadecenol(14)

4′-methoxy-2-ethyl,2-(4-methoxyphenyl) acetophenone 13 (710 mg, 2.5 mmol, prepared from desoxyanisoin, ethyl bromide and LDA by a known method) in THF (10 ml) are added, under argon, to Grignard reagent prepared from 11-bromo-tetrahydropyranyl undecanol (6.6 g, 19.7 mmoles) and magnesium (0.6 g, 24.7 mmoles) and THF (10 ml). The mixture was stirred for 18 hours, then acidified with 1N HCl and extracted three times with ether. The organic phase was washed with water (X3), dried over anhydrous magnesium sulfate, and evaporated under reduced pressure. The residue was chromatographed on Silica gel (Kieselgel, 60F254, Merck, 0.063–0.200 mm, 100 g). Elution with a mixture of hexane-ethyl acetate (9:1 v/v) gave 12,13-Bis-(4-methoxyphenyl)-tetrahydropyranyl pentadecan-1,12-diol (991 mg, 76%) as a mixture of diastereoisomers; colorless oil, IR $\nu_{max}$ (neat) 3480, 1600 cm$^{-1}$; $^1$H-NMR ($\delta$, CDCl$_3$); 0.62 (3H, t, J=7.3 Hz, CH$_2$CH$_3$), 2.73 (1H, 2d, J=9.7 Hz, —CHCH$_2$CH$_3$), 3.25–4.00 (4H, m, —CH$_2$OCHOCH$_2$—), 3.76 and 3.79 (6H, 2s, —OCH$_3$), 4.57 (1H, t, J=1.1 Hz, —O$_3$—CH—CH$_2$) and 6.71–7.30 (8H, m,H-Ar)ppm. MS m/e=523 (M$^+$-H$_2$O).

The above diastereoisomers (920 mg, 1.8 mmol) dissolved in methanol (30 ml) and 5N HCl (5 ml) was refluxed for 1 hour, then collected, and extracted three times with ether. The organic layer was washed with water, dried over anhydrous magnesium sulfate, evaporated under reduced pressure to dryness and finally chromatographed on silica gel (Kiesegel, 60F254, 0.063–0.200 mm, Merck, 100 g). Elution with a mixture of hexane-ethyl acetate (7:3 v/v) gave 12,13-Bis-(4-methoxyphenyl)-11-pentadecenol (710 mg, 65% from compound 13), colorless oil, IR $\nu_{max}$ (neat), 3340, 1600, 1030 cm$^{-1}$, UV $\lambda_{max}$ (log $\epsilon$)=231 (4.27) nm; $^1$H-NMR ($\delta$, CDCl$_3$), 0.88 (3H, t, J=7.3 Hz, —CH$_2$CH$_3$), 3.30 (1H,t,J=9.7 Hz, —CH—CH$_2$, CH$_3$), 3.63 (2H,t, J=6.6 Hz, —CH$_2$OH), 3.76 and 3.78 (6H, 2s, —OCH$_3$), 5.51 (1H, t, J=8.8 Hz,1 —C≡CH—) and 6.63–7.10 8H, m, H-Ar) ppm; MS m/e=438 (M$^+$).

N-butyl, N-methyl-12,12-Bis-(4-methoxyphenyl)-11-pentadecenoic amide (15)

To a cooled solution of alcohol 14 (710 mg, 1.56 mmol) in acetone (17 ml) was added Jones' reagent (8N-chromic acid solution, 0.77 ml). After 30 minutes, isopropanol (5 ml) was added and the mixture was poured in water and extracted three times with ethyl acetate. The organic layer was washed twice with brine, dried over magnesium sulfate and evaporated to dryness. The crude 12,13-Bis-(4-methoxyphenyl)-11-pentadecenoic acid was used in the next step without purification. To its solution in anhydrous methylene chloride (4 ml) at −10° C. was added, under stirring, triisobutylamine (470 µl, 1.96 mmol) and isobutylchloroformate (280 µl, 2.1 mmol). After 40 minutes, N-methylbutylamine (1.5 ml) was added and the mixture was stirred at room temperature during 1 hour. Methylene chloride (50 ml) was added. The organic solution was washed with 1N HCl, saturated sodium bicarbonate solution and water (3X), dried on magnesium sulfate and evaporated to dryness. The residue was purified by "flash chromatography" on silica gel (Kieselgel 60, Merck, unter 0.063 mm, 50 g). Elution with a mixture of hexane-ethyl acetate (4:1 v/v) gave N-butyl, N-methyl-12,13-Bis (4-methoxyphenyl)-11-pentadecenoic amide (15), (549 mg, 68%) colorless oil; IR $\nu_{max}$ (neat), 1640, 1600 cm$^{-1}$; UV $\lambda_{max}$(log $\epsilon$)=230 (4.39) nm; $^1$H-NMR ($\delta$, CDCl$_3$), 0.85–0.98 (6H, m, 2-CH$_2$CH$_3$), 2.27 (2H, t, J=7.1 Hz, CH$_3$CON), 2.91 and 2.96 (3H, 2s, —NCH$_3$), 3.25–3.36 (3H, m, —NCH$_3$— and CH$_3$CH$_3$CH-), 3.77 and 3.78 (6H, 2s, OCH$_3$), 5.50 (1H, J=7.1 Hz, —C≡CH—) and 6.69–7.01 (8H, m, H-Ar) ppm; MS m/e=521 (M+).

N-butyl, N-methyl-12,13-Bis-(4-hydroxyphenyl)-12-pentadeconic amide ("EM-142", compound 16 with x=10)

To the above dimethoxy amide 15 (117 mg, 0.22 mmol) in CH$_2$Cl$_2$ (1 ml) at 0° C. was added, under argon, 1.0 M borane tribromide (675 µl). The solution was stirred for 1 hour, then poured into water and extracted with ether (3X). The organic solution was washed with water, dried on magnesium sulfate, and evaporated to dryness. The residue was purified by "Flash chromatography" on silica gel (Kieselgel 60, Merck, unter 0.063 mm, 30 g). Elution with a mixture of hexane-ethyl acetate (4:1 v/v) gave N-butyl, N-methyl-12,13-Bis (4-hydroxyphenyl)-12-pentadeconic amide ("EM-142", compound 16 with X=10) (34 mg, 31%), colorless oil, IR $\nu_{max}$(neat) 3300, 1600 cm$^{-1}$; UV $\nu_{max}$ (log $\epsilon$)=235 (4.25) nm; $^1$H-NMR ($\delta$, CDCl$_3$), 0.76 (3H, t, J=7.3 Hz, —CH$_3$CH$_3$), 0.96 (3H, t, J=7.3 Hz, N (CH$_2$)$_3$CH$_3$), 2.05–2.20 (4H, m, CH$_2$-C≡C—CH$_2$—), 2.35 (2H, t, J=7.0 Hz, —CH$_3$ CON—), 2.97 and 3.00 (3H, s, —NCH$_3$), 3.29 and 3.41 (2H, 2t, J=7.3 Hz, —N—CH$_3$—), and 6.59–7.09 (8H, m, H-Ar) ppm; MS m/e=493 (M+).

Scheme 4
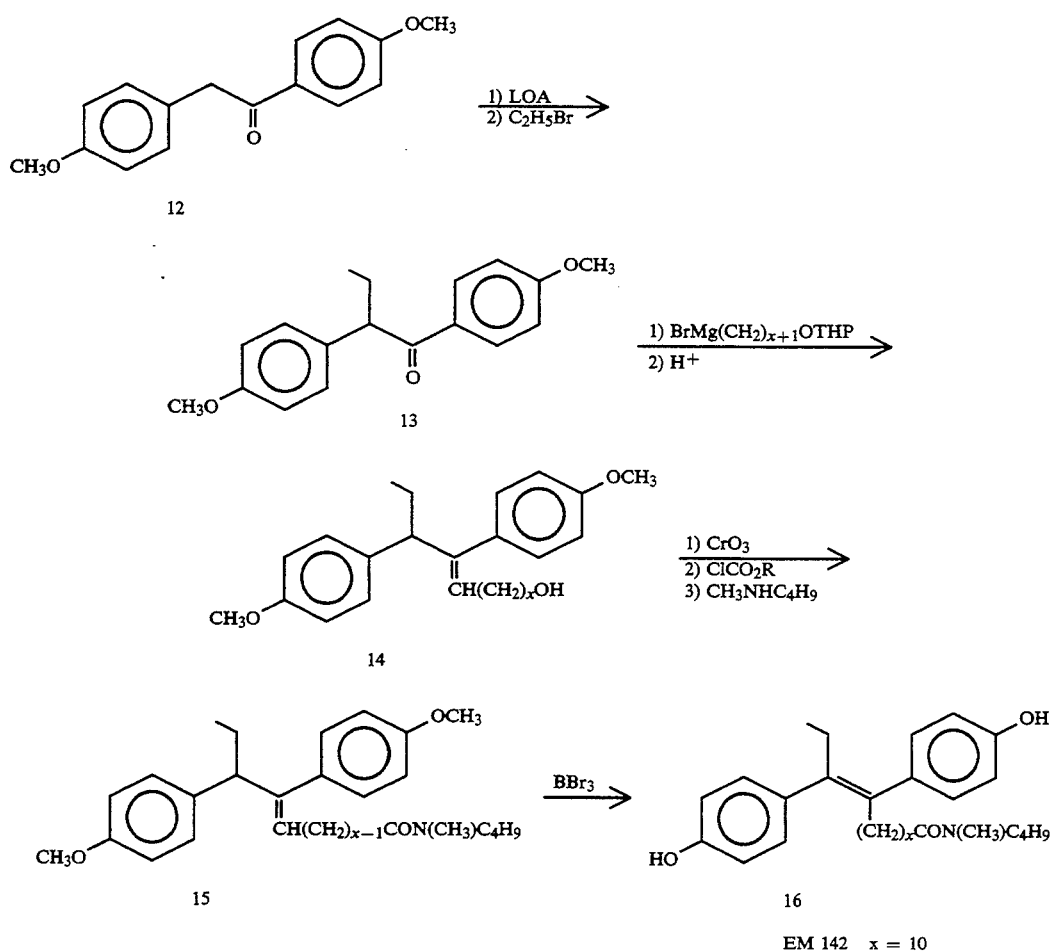
EXAMPLE 5
N-butyl, N-methyl (ω-2) p-hydroxyphenyl (ω-1)-(hydroxy cyclohexa-4-yl) alkylamide
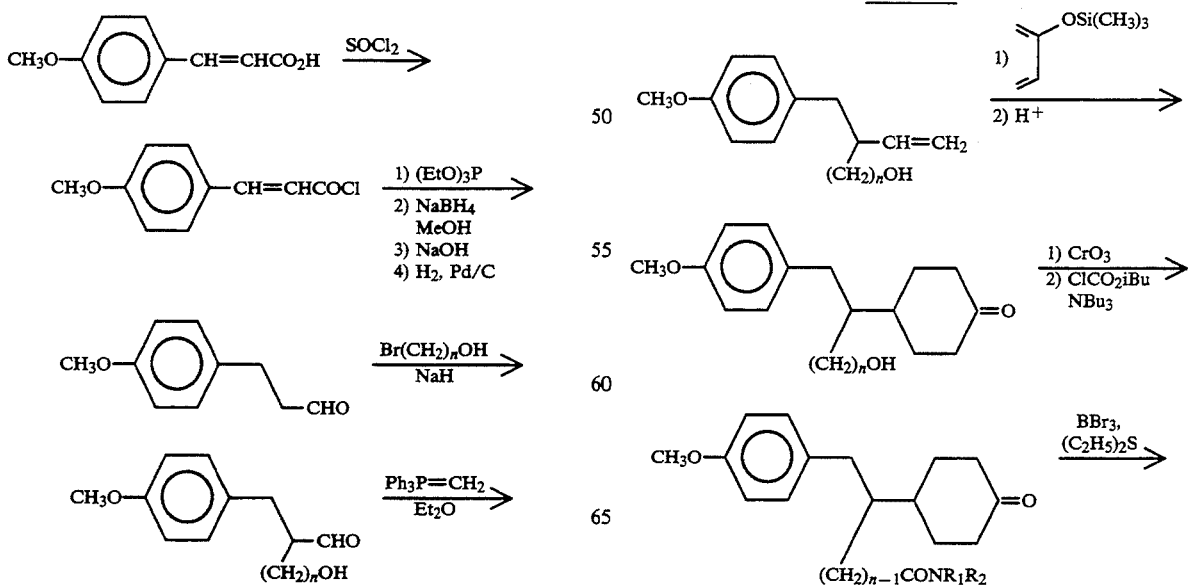

-continued
Scheme 5

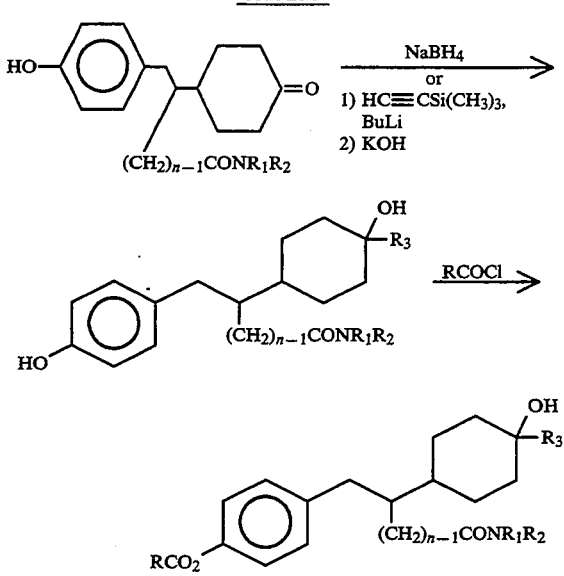

The compounds synthesized above have been tested and have been found to be effective inhibitors of the activity of enzymes which catalyze sex steroid formation. In order to test this inhibition, the effect of the above-synthesized compounds on the 17β-hydroxysteroid dehydrogenase-catalyzed conversion of estradiol to estrone was observed. The reaction was followed by monitoring-formation of NADH at 340 nm (the rate of conversion of the cofactor NAD to NADH varies directly with the rate of estradiol conversion to estrone). The ability of compounds of the invention to inhibit this reaction is indicative of their ability to inhibit the estrogen-forming reverse reaction because both reactions are catalyzed by 17β-hydroxysteroid dehydrogenase (Thomas et al., J. Biol. Chem. 258: 11500–11504, 1983).

To test the effect of EM 139, 17β-hydroxysteroid dehydrogenase (17β-HSD) was purified to homogeneity from human placenta. A reaction vessel was prepared containing 1 μg 17β-HSD, 5 mM NAD, 20 μM 17β-estradiol, and the concentrations of the test compound EM 139 indicated along the X-axis of FIG. 1 in 1.0 ml of a mixture of Tris-CHl (50 mM), EDTA (2 mM), NaN₃ (5 mM). The pH was 7.5. The reaction was allowed to proceed at 25° C. for 15 min. Formation of NADH was measured at 340 nm. As shown by FIG. 1, increasing concentrations of EM 139 significantly inhibited the reaction.

Figure 2:
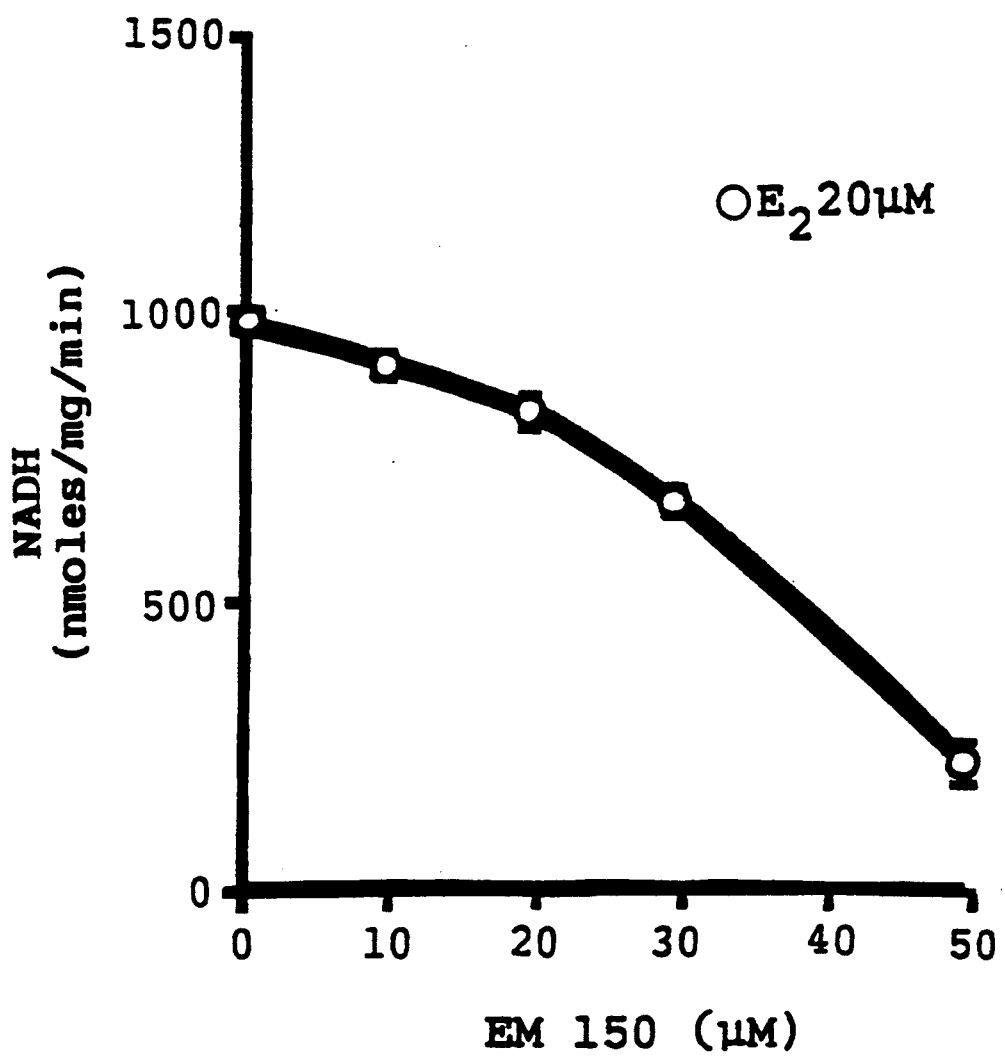
FIG. 2 is a graph showing the inhibitory effect of 17β-hydroxy-17α-(12-iododecynyl)-Δ⁴-androsten-3-one ("EM 150") on 17β-hydroxysteroid dehydrogenase activity at different concentrations.

To test the effect of EM 150, 17β-hydroxysteroid dehydrogenase (17β-HSD) was purified to homogeneity from human placenta. A reaction vessel was prepared containing 1 μg 17β-HSD, 5 mM NAD, 20 μM 17β-estradiol, and the concentrations of the test compound EM 139 indicated along the X-axis of FIG. 2 in 1.0 ml of a mixture of Tris-HCl (50 mM), EDTA (2 mM), MaN₃ (5 mM). The pH was 7.5. The reaction was allowed to proceed at 25° C. for 15 min. Formation of NADH was measured at 340 nm. As shown by FIG. 2, increasing concentrations of EM 150 significantly inhibited the reaction.

Figure 3:
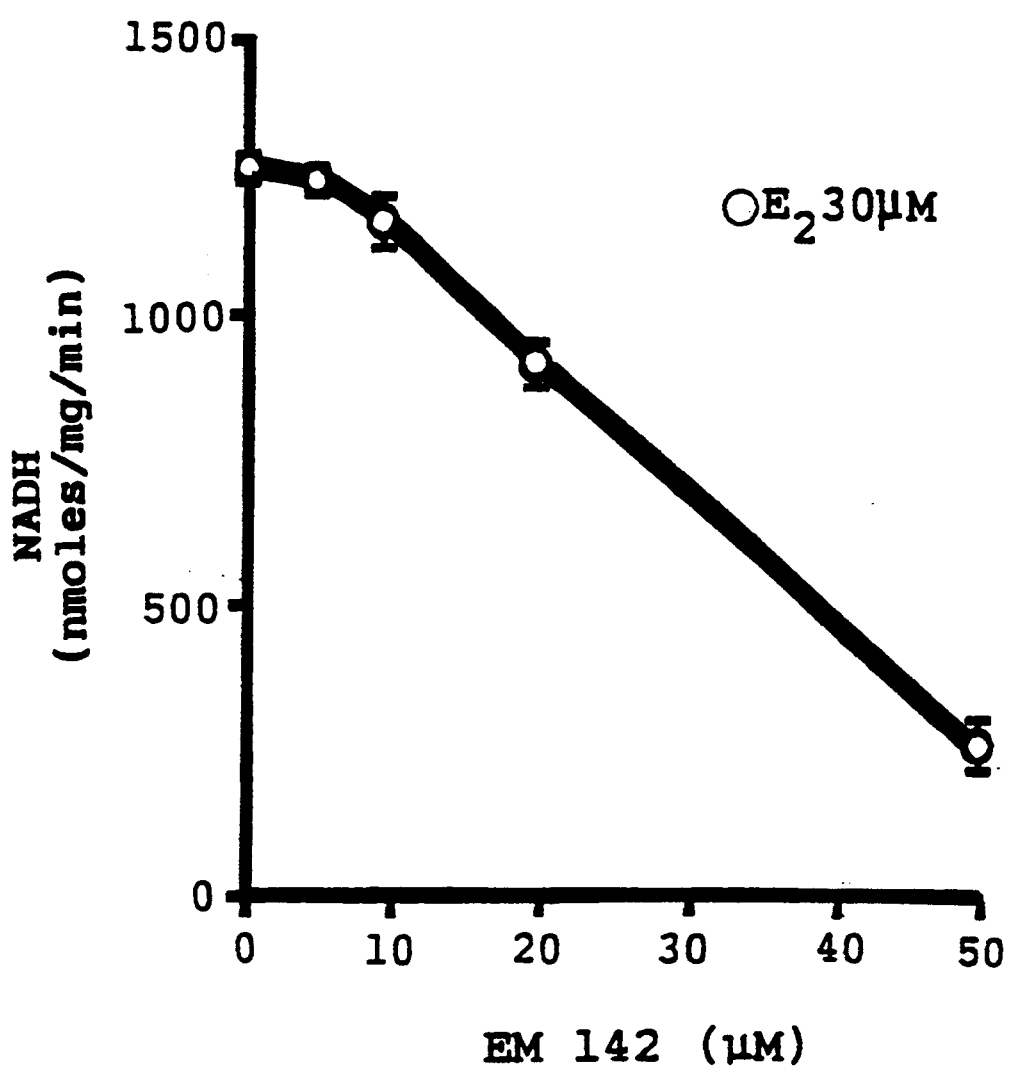
FIG. 3 is a graph showing the inhibitory effect of N-butyl, N-methyl-12,13-bis(4-hydroxyphenyl)-12-pentadecenamide ("EM 142") on 17-hydroxysteroid dehydrogenase activity at different concentrations.

To test the effect of EM 142, 17β-hydroxysteroid dehydrogenase (17β-HSD) was purified to homogeneity from human placenta. A reaction vessel was prepared containing 1 μg 17β-HSD, 5 mM NAD, 20 μM 17β-estradiol, and the concentrations of the test compound EM 142 indicated along the X-axis of FIG. 3 in 1.0 ml of a mixture of Tris-HCl (50 mM), EDTA (2 mM), NaN₃ (5 mM). The pH was 7.5. The reaction was allowed to proceed at 25° C. for 15 min. Formation of NADH was measured at 340 nm. As shown by FIG. 3, increasing concentrations of EM 142 significantly inhibited the reaction.

The terms and descriptions used herein are preferred embodiments set forth by way of illustration only, and are not intended as limitations on the many variations which those of skill the art will recognize to be possible in practicing the present invention as defined by the following claims.

What is claimed is:

1. A method for inhibiting sex steroid formation comprising administering to a warm-blooded patient in need of such inhibition, a therapeutically effective amount of a compound of the formula:

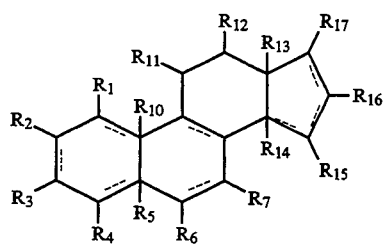

wherein the dotted lines represent optional double bonds; wherein the A-ring is optionally aromatic;
wherein $R_1$, $R_2$ and $R_4$ are independently selected from the group consisting of hydrogen, hyroxyl, alkylsulfonyl(lower)alkoxy, arylsulfonyl(lower)alkoxy, halogen, lower alkyl, lower alkoxy, lower alkylsilyl, amino and nitro;
wherein $R_3$ is selected from the group consisting of hydrogen, hydroxyl, halogen, lower alkyl, methoxy, ethoxy, propoxy, hydroxyethoxy, lower alkoxy, acetoxy, propionyloxy, butyryloxy, oenanthoyloxy, cypionoyloxy, trans-4-n-butyl-cyclohexanecarbonoyloxy, ($C_2$-$C_{20}$)alkanoyloxy, lower alkoxy carbonyloxy, carboxy, ($C_3$-$C_{20}$)alkenoyloxy, ($C_3$-$C_{20}$)alkynoyloxy, ($C_7$-$C_{10}$)aroyloxy or a divalent common species formed jointly by $R_{3(\alpha)}$ and $R_{3(\beta)}$, said divalent common speices being selected from the group consisting of =O, =S, =NR_{36} or =NOR_{36} wherein $R_{36}$ is hydrogen or lower alkyl;
wherein $R_5$ and $R_{10}$ are absent or selected from the group consisting of hydrogen and lower alkyl;
wherein $R_6$ is selected from the group consisting of hydrogen, halogen, lower alkyl, amino and nitrile;
wherein $R_7$ is in α position and is hydrogen, hydroxyl, halogen, lower alkyl, lower alkoxy, lower alkylsilyl, amino, nitrile, nitro, nitroso, alkylsulfonyl, arylsulfonyl, lower alkylamino, dilower alkylamino, or is represented by the formula $A^1$-[Y-$A^{11}$]$_u$—X—$R_{21}$, wherein:
u is an integer from 0 to 5; wherein $A^1$ and $A^{11}$ may be the same or different and are selected from the group consisting of a bond, straight- or branched-chain alkylene, straight- or branched-chain alkynylene, straight- or branched-chain alkenylene, and fluoro-substituted analogs of the foregoing, wherein $R^1$ and $A^{11}$ together have a total of from 3 to 30 carbon atoms, and Y is selected from the group consisting of —O—, —S—, —Se—, —SO—, —$SO_2$—, —CO—, —$NR_{22}$—, —$SiR_{22}R_{22}$—, —$CR_{22}OR_{22}$—$NR_{22}CO$—, —$NR_{22}CS$—, —$CONR_{22}$—, —$CSNR_{22}$—, —COO—, —COS—, —SCO—, —CSS—, —SCS—, —OCO— and phenylene ($R_{22}$ being hydrogen or lower alkyl); $R_{21}$ is selected from the group consisting of hydrogen, straight- or branched-chain lower alkyl, lower alkenyl or lower alkynyl, ($C_3$-$C_7$)cycloalkyl, halogeno(lower)alkyl, carboxy(lower)alkyl, (lower)alkoxycarbonyl(lower)alkyl, ($C_6$-$C_{10}$)aryl, ($C_7$-$C_{11}$)arylalkyl, di(lower)alkylamino(lower)alkyl and fluoro-substituted analogs of the foregoing, and wherein X is —$CONR_{23}$—, —$CSNR_{23}$—, —$NR_{24}CO$—, —$NR_{24}CS$—, —$NR_{24}CONR_{23}$—,

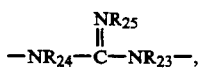

—$SO_2NR_{23}$—, —CSS—, —SCS—, —$NR_{23}$—, —(NO)$R_{23}$—, —(PO)$R_{23}$—, —$NR_{24}CO$—, —$NR_{24}SO_2$—, —S—, —SO— or —$SO_2$—, (wherein $R_{23}$ is selected from the group consisting of hydrogen, lower alkyl, and a species which, together with $R_{21}$, forms a saturated or unsaturated heterocyclic ring having at least one nitrogen atom and, optionally, a second heteroatom selected from the group consisting of oxygen, sulfur, silicon, selenium, nitrogen and fluoro-substituted analogs of the foregoing, wherein $R_{24}$ is hydrogen or lower alkyl and wherein $R_{25}$ is hydrogen, nitrile or nitro) ($XR_{21}$ may form a tetrazole ring);
wherein $R_{11}$ is selected from the group consisting of hydrogen, lower alkyl, lower alkenyl, lower alkynyl, ($C_6$-$C_{10}$)aryl, alkylsulfonyl, arylsulfonyl, a substituted 5-to-7 member heterocyclic ring having at least one heteroatom (selected from oxygen, sulfur, silicon, selenium, nitrogen), —($CH_2$)$_s$W (wherein W is nitrile, hydroxyl, azido, nitroso, nitro, thionitrile, halogen, alkylsulfonyl or arylsulfonyl, and s is an integer from 1 to 6), $OR_{26}$ (wherein $R_{26}$ is hydrogen, lower alkyl or ($C_6$-$C_{10}$)aryl), $DR_{27}$ (wherein D is —Se—, —$NR_{26}$, —S— or —O—, and $R_{27}$ is hydrogen, lower alkyl), =O, =S, =Se, =$NR_{28}$ (wherein $R_{28}$ is hydrogen or lower alkyl;
wherein $R_{12}$ and $R_{13}$ are independently hydrogen or lower alkyl;
wherein $R_{14}$ is selected from the group consisting of hydrogen, hydroxyl, nitrile, nitro, nitroso, halogen, lower alkyl, lower alkoxy, lower alkyseleno, lower alkylamino or diloweralkylamino; or $R_{14}$ and $R_{15}$ together are —$CH_2$—, —CHX—, —$CX_2$—, (X=halogen, carboxyl or alkoxycarbonyl), —O—, —S—, —Se—, >N-CN, >$NR_{29}$ and >$NCO_2R_{29}$ wherein $R_{29}$ is hydrogen or lower alkyl;
wherein $R_{15}$ is selected from the group consisting of hydrogen, hydroxyl, nitro, nitroso, halogen, lower alkyl, lower alkenyl, lower alkynyl, lower alkoxy, lower alkylseleno, lower alkylamino, di(lower)alkylamino, nitrile, azido, arylseleno, $AXR_{21}$, $A_1$-[Y-$A^{11}$]$_u$-X-$R_{21}$ or $R_{15}$ and $R_{16}$ together are —$CH_2$—, —CHX—, —$CX_2$—, (X=halogen, carboxyl or alkoxycarbonyl), —O—, —S—, —Se—, >N-CN, >$NR_{29}$ and >$NCO_2R_{29}$ wherein $R_{29}$ is hydrogen or lower alkyl;
wherein $R_{16}$ is selected from the group consisting of hydrogen, nitroso, halogen, lower alkyl, carboxyl, lower alkoxy, lower alkylseleno, lower alkylamino, nitrile, azido, arylseleno, lower alkylseleno, di(lower)alkylamino, $AXR_{21}$, or $A^1$-[Y-$A^{11}$]$_u$-X-$R_{21}$, $R_{16(\alpha)}$ and $R_{16(\beta)}$ together are =$CG_2$, where G is hydrogen, halogen, lower alkyl, lower alkenyl, lower alkynyl, nitrile, alkoxycarbonyl, alkylcarbonyl and carboxyl;
wherein $R_{17(\alpha)}$ is selected from the group consisting of hydrogen, hydroxyl, lower alkyl, halogeno(lower)alkyl, $AXR_2$, $A^1$-[Y-$A^{11}$]$_u$X-$R_{21}$, $B^1$-T-$R_{30}$ wherein:
$B^1$ is straight- or branched-chain ($C_1$-$C_{12}$)alkylene, ($C_2$-$C_{12}$)alkynylene, ($C_2$-$C_{12}$)alkenylene; T is —O—, —$NR_{31}$, —Se—, —S— or S-S and $R_{30}$ and $R_{31}$ are independently hydrogen, lower alkyl, or $R_{30}$ and $R_{31}$, together are ($C_3$-$C_7$)cycloalkyl, ($C_5$-$C_7$)cycloalkenyl, ($C_3$-$C_7$)cycloalkyl or ($C_5$-$C_7$)cycloalkenyl having one or more hydrogen atoms replaced by halogen atoms, —HC=$CHR_{32}$ and —C≡$CR_{33}$ wherein:
$R_{32}$ and $R_{33}$ are independently hydrogen, halogen, tri(lower)alkylsilyl, carboxyl, carbonyl, lower alkoxy, nitrile, sulfinyl lower alkyl, $AXR_{21}$, $A^1$-[Y-$A^{11}$]$_u$-X-$R_{21}$ or a species represented by the formula:

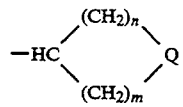

a wherein n and m are independently 0 to 6 and Q is —Se—, —$SiH_2$—, —S—, —O— or —$NR_{34}$— wherein $R_{34}$ is hydrogen, lower alkyl or ($C_1$-$C_7$)alkanoyl; or a species represented by the formula:

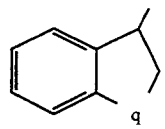

b wherein q is —$CH_2$—, —S—, —O— or —$NR_{35}$—
wherein $R_{35}$ is hydrogen or lower alkyl;
wherein $R_{17(\beta)}$ is selected from the group consisting of hydrogen, hydroxyl, halogen, 1-oxo-2-propoynyl, 1-hydroxy-2-propynyl, alkoxy, ($C_1$-$C_{17}$)alkanoyloxy, ($C_3$-$C_7$)alkenyloxy, ($C_3$-$C_7$)alkynoyloxy, alkenyloxy, cycloalkenyloxy, 1-alkyloxy-alkyloxy, 1-alkyloxy cycloalkyloxy, alkylsilyloxy and a divalent common species formed jointly by $R_{17(\alpha)}$ and $R_{17(\beta)}$, said divalent common species being selected from the group consisting of =O, =S, =$NR_{36}$ or =$NOR_{36}$ wherein $R_{36}$ is hydrogen or lower alkyl, wherein at least one or $R^7$, $R^{16}$ or $R^{17}$ is $A^1$-[Y-$A^{11}$-]$_u$X$R^{21}$.

2. The method of claim 1 wherein androgen formation is inhibited.

3. The method of claim 1 wherein estrogen formation is inhibited.

4. The method of claim 1 wherein said compound is administered in the form of parenteral controlled-release composition at a daily release does of from 5 to 1250 mg per day.

5. The method of claim 1 where said compound is administered in the form of oral composition at a daily release dose of from 5 to 1250 mg per day.

6. A method according to claim 1 wherein the testicular or ovarian secretions of the patient are inhibited by surgical or chemical means.

7. The method of claim 1 wherein said compound is

8. A method of claim 1 wherein said compound is

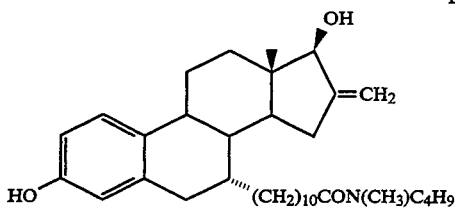
"EM 186"

9. The method of claim 1 wherein said compound is

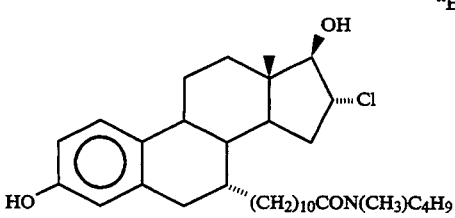
"EM 139"

10. The method of claim 1, wherein said compound

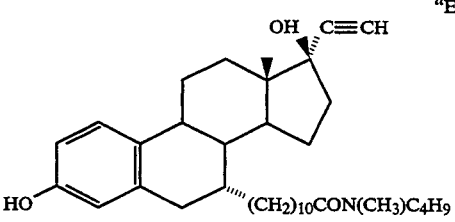
"EM 104"

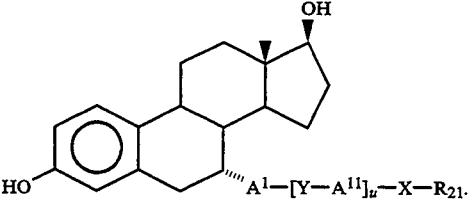

11. A pharmaceutical composition comprising a pharmaceutically effective diluent or carrier and a therapeutically effective amount of a compound of the formula:

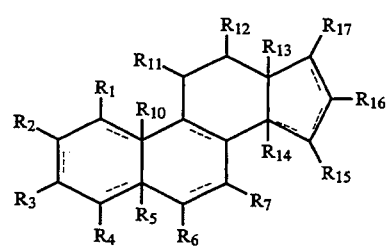   I wherein the dotted lines represent optional double bonds; wherein the A-ring is optionally aromatic;

whrein $R_1$, $R_2$ and $R_4$ are independently selected from the group consisting of hydrogen, hydroxyl, alkylsulfonyl(lower)alkoxy, arylsulfonyl(lower)alkoxy, halogen, lower alkyl, lower alkoxy, lower alkylsilyl, amino and nitro;

wherein $R_3$ is selected from the group consisting of hydrogen, hydroxyl, halogen, lower alkyl, methoxy, ethoxy, propoxy, hydroxyethoxy, lower alkoxy, acetoxy, propionyloxy, butyryloxy, oenanthoyloxy, cypionoyloxy, trans-4-n-butyl-cyclohexanecarbonoyloxy, ($C_2$-$C_{20}$) alkanoyloxy, lower alkoxy carbonyloxy, carboxy, ($C_3$-$C_{20}$) alkenoyloxy, ($C_3$-$C_{20}$) alkynoyloxy, ($C_7$-$C_{10}$) aroyloxy or a divalent common species formed jointly by $R_{3(\alpha)}$ and $R_{3(\beta)}$, said divalent common species being selected from the group consisting of =O, =S, =$NR_{36}$ or =$NOR_{36}$ wherein $R_{36}$ is hydrogen or lower alkyl;

wherein $R_5$ and $R_{10}$ are absent or selected from the group consisting of hydrogen and lower alkyl;

wherein $R_6$ is selected from the group consisting of hydrogen, halogen, lower alkyl, amino and nitrile;

wherein $R_7$ is in α position and is hydrogen, hydroxyl, halogen, lower alkyl, lower alkoxy, lower alkylsilyl, amino, nitrile, nitro, nitroso, alkylsulfonyl, arylsulfonyl, lower alkylamino, dilower alkylamino, or is represented by the formula $A^1$-$[Y$-$A^{11}]_u$—X—$R_{21}$, wherein:

u is an integer from 0 to 5; wherein $A^1$ and $A^{11}$ may be the same or different and are selected from the group consisting of a bond, straight- or branched-chain alkylene, straight- or branched-chain alkynylene, straight- or branched-chain alkenylene, and fluoro-substituted analogs of the foregoing, wherein $A^1$ and $A^{11}$ together have a total of from 3 to 30 carbon atoms, and Y is selected from the group consisting of —O—, —S—, —Se—, —SO—, —SO$_2$—, —CO—, —NR$_{22}$—, —SiR$_{22}$R$_{22}$, —CR$_{22}$OR$_{22}$—, —NR$_{22}$—CO—, —NR$_{22}$CS—, —CONR$_{22}$—, —CSNR$_{22}$—, —COO—, —COS—, —SCO—, —CSS—, —SCS—, —OCO— and phenylene ($R_{22}$ being hydrogen or lower alkyl); $R_{21}$ is selected from the group consisting of hydrogen, straight- or branched-chain lower alkyl, lower alkenyl or lower alkynyl, ($C_3$-$C_7$) cycloalkyl, halogeno(lower)alkyl, carboxy(lower)alkyl, (lower) alkoxycarbonyl(lower)alkyl, ($C_6$-$C_{10}$) aryl, ($C_7$-$C_{11}$) aryl-alkyl, di(lower) alkylamino(-lower)alkyl and fluoro-substituted analogs of the foregoin, and wherein X is —CONR$_{23}$—, —CSNR$_{23}$—, —NR$_{24}$CO—, —NR$_{24}$CS—, —NR$_{24}$CONR$_{23}$—, $$-NR_{24}-\overset{NR_{25}}{\underset{\|}{C}}-NR_{23}-,$$

—SO$_2$NR$_{23}$—, —CSS—, —SCS—, —NR$_{23}$—, —(NO)R$_{23}$—, —(PO)R$_{23}$—, —NR$_{24}$COO—, —NR$_{24}$SO$_2$—, —S—, —SO— or —SO$_2$—, (where $R_{23}$ is selected from the group consisting of hydrogen, lower alkyl, and a species which, together with $R_{21}$, forms a saturated or unsaturated heterocyclic ring having at least one nitrogen atom and, optionally, a second hereroatom selected from the group consisting of oxygen, sulfur, silicon, selenium, nitrogen and fluoro-substituted analogs of the foregoing, where $R_{24}$ is hydrogen or lower alkyl and wherein $R_{25}$ is hydrogen, nitrile or nitro) (XR$_{21}$ may form a tetrazole ring);

wherein $R_{11}$ is selected from the group consisting of hydrogen, lower alkyl, lower alkenyl, lower alkynyl, ($C_6$-$C_{10}$) aryl, alkylsulfonyl, arysulfonyl, a substituted 5-to-7 member heterocyclic ring having at least one heteroatom (selected from oxygen, sulfur, silicon, selenium, nitrogen), —(CH$_2$)$_s$W (wherein W is nitrile, hydroxyl, azido, nitroso, nitro, thionitrile, halogen, alkylsulfonyl or arylsulfonyl, and s is an interger from 1 to 6), OR$_{26}$ (wherein R$_{26}$ is hydrogen, lower alkyl or (C$_6$-C$_{10}$) aryl), DR$_{27}$ (wherein D is —Se—, —NR$_{26}$, —S— or —O—, and R$_{27}$ is hydrogen, lower alkyl), =O, =S, =Se, =NR$_{28}$ (wherein R$_{28}$ is hydrogen or lower alkyl; wherein R$_{12}$ and R$_{13}$ are independently hydrogen or lower alkyl; wherein R$_{14}$ is selected from the group consisting of hydrogen, hydroxyl, nitrile, nitro, nitroso, halogen, lower alkyl, lower alkoxy, lower alkyseleno, lower alkylamino or diloweralkylamino; or R$_{14}$ and R$_{15}$ together are —CH$_2$—, —CHX—, —CX$_2$—, (X=halogen, carboxyl or alkoxycarbonyl), —O—, —S—, —Se—, >N-CN, >NR$_{29}$ and >NCO$_2$R$_{29}$ wherein R$_{29}$ is hydrogen or lower alkyl;

wherein R$_{15}$ is selected from the group consisting of hydrogen, hydroxyl, nitro, nitroso, halogen, lower alkyl, lower alkenyl, lower alkynyl, lower alkoxy, lower alkylseleno, lower alkylamino, di(lower) alkylamino, nitrile, azido, arylseleno, AXR$_{21}$, A$_1$-[Y-A$^{11}$]$_u$—X—R$_{21}$ or R$_{15}$ and R$_{16}$ together are —CH$_2$—, —CHX—, —CX$_2$—, (X=halogen, carboxyl or alkoxycarbonyl), —O—, —S—, —Se—, >N-CN, >NR$_{29}$ and >NCO$_2$R$_{29}$ wheren R$_{29}$ is hydrogen or lower alkyl;

wherein R$_{16(\alpha)}$ is selected from the group consisting of chlorine, fluorine, bromine, iodine, R$_{16(\alpha)}$ together with or R$_{16(\beta)}$ is =CG$_2$.

wherein R$_{17(\alpha)}$ is selected from the group consisting of hydrogen, hydroxyl, lower alkyl, halogeno(lower)alkyl, AXR$_2$, A$^1$-[Y-A$^{11}$]$_u$X—R$_{21}$, B$^1$-T-R$_{30}$ wherein:

B$^1$ is straight- or branched-chain (C$_1$-C$_{12}$) alkylene, (C$_2$-C$_{12}$) alkynylene, (C$_2$-C$_{12}$) alkenylene; T is —O—, —NR$_{31}$, —Se—, —S— or S—S and R$_{30}$ and R$_{31}$ are independently hydrogen, lower alkyl, or R$_{30}$ and R$_{31}$, together are (C$_3$-C$_7$) cycloalkyl, (C$_5$-C$_7$) cycloalkyenyl, (C$_3$-C$_7$) cycloalkyl or (C$_5$-C$_7$) cycloalkenyl having one or more hydrogen atoms replaced by halogen atoms, —HC=CHR$_{32}$ and —C≡CR$_{33}$ wherein:

R$_{32}$ and R$_{33}$ are independently hydrogen, halogen, tri(lower)alkylsily, carboxyl, carbonyl, lower alkoxy, nitrile, sulfinyl lower alkyl, AXR$_{21}$, A$^1$-[Y-A$^{11}$]$_u$—X—R$_{21}$ or a species represented by the formula:

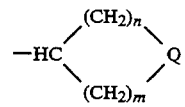

a wherein n and m are independently 0 to 6 and Q is —Se—, —SiH$_2$—, —S—, —O— or —NR$_{34}$— wherein R$_{34}$ is hydrogen, lower alkyl or (C$_1$-C$_7$)alkanoyl; or a species represented by the formula:

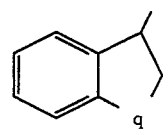

b wherein q is —CH$_2$—, —S—, —O— or —NR$_{35}$— wherein R$_{35}$ is hydrogen or lower alkyl;

wherein R$_{17(\beta)}$ is selected from the group consisting of hydrogen, hydroxyl, halogen, 1-oxo-2-propynyl, 1-hydroxy-2-propynyl, alkoxy, (C$_1$-C$_7$)alkanoyloxy, (C$_3$-C$_7$)alkenoyloxy, (C$_3$-C$_7$)alkynoyloxy, alkenyloxy, cycloalkenyloxy, 1-alkyloxy-alkyloxy, 1-alkyloxy cycloalkyloxy, alkylsilyloxy and a divalent common species formed jointly by R$_{17(\alpha)}$ and R$_{17(\beta)}$, said divalent common species being selected from the group consisting of =O, =S, =NR$_{36}$ or =NOR$_{36}$ wherein R$_{36}$ is hydrogen or lower alkyl, wherein at least one or R$^7$, R$^{16}$ or R$^{17}$ is A$^1$-[Y-A$^{11}$]$_u$XR$^{21}$.

* * * * *

UNITED STATES PATENT AND TRADEMARK OFFICE
CERTIFICATE OF CORRECTION

PATENT NO. : 5,364,847                          Page 1 of 10
DATED      : November 15, 1994
INVENTOR(S): Fernand Labrie, et al.

It is certified that error appears in the above-indentified patent and that said Letters Patent is hereby corrected as shown below:

On title page,
Item [56], under FOREIGN PATENT DOCUMENTS, line 2, delete in its entirety.

column 1, line 28, change "Endodrin." to --Endocrin.--;
line 38, after "al.," insert --J. Steroid Biochem., 20(6B),--;
line 39, after "al.," insert --Ann. Meeting of the Endocr. Soc.,--;
line 40, after "al.," insert --J. Steroid Biochem., 20(6B),--;
line 45, delete ":88".

column 2, line 5, change "1902" to --1982--;
line 10, after "8221" insert ---8228,--;
line 18, change "Klijin" to --Klijn--; after "(6B)" insert --No A33 Abstract--;
line 23, change "Jordon" to --Jordan--; change "Endocrinolgoy" to --Endocrinology--; after "4," insert --pp. 1717-1726--;
line 24, before "Important" insert --Labrie et al.,--;
line 39, change "1987" to --1988--;
line 40, change "4432-4438" to --4452-4458--.

column 1, line 7, change "588" to --538--;
line 8, change "1988" to --1987--.

UNITED STATES PATENT AND TRADEMARK OFFICE
CERTIFICATE OF CORRECTION

PATENT NO. : 5,364,847                           Page 2 of 10
DATED      : November 15, 1994
INVENTOR(S): Fernand Labrie, et al.

It is certified that error appears in the above-indentified patent and that said Letters Patent is hereby corrected as shown below:

```
column 2, line  5,  after "al.," insert
                    --Steroids--.

Column 1, line 18,  change "casuign" to --causing--;
         line 37,  change "17α" to --17β--;
         line 56,  change "17" to --17β--; and
         line 63,  after "another" insert
                    --object--.

Column 2, line  1,  change "noval" to --novel--;
         line  4,  change "posiions" to
                    --positions--;
         line 48,  change "R₅" to --R₆--;
         line 54,  change "R₁₁" to --R₂₁--; and
         line 56,  change "A²" to --A¹--.

Column 3, line  5,  delete second occurrence of
                    "halogeno (lower) alkyl,";
         line 23,  change "aption-" to --option---;
         line 27,  after "alkyl)" insert --and--;
         line 35,  change "5" to --s--;
         line 37,  change "S" to --s--;
         line 41,  change "26" to --28--;
         line 47,  change "CH₃" to --CH₂--;
         line 49,  change "NR₃₉" to --NR₂₉--;
                    change "NCO₃" to --NCO₂--; and,
         line 55,  change "A₁" to --A¹--.
```

UNITED STATES PATENT AND TRADEMARK OFFICE
CERTIFICATE OF CORRECTION

PATENT NO. : 5,364,847　　　　　　　　　　Page 3 of 10

DATED : November 15, 1994

INVENTOR(S) : Fernand Labrie, et al.

It is certified that error appears in the above-indentified patent and that said Letters Patent is hereby corrected as shown below:

Column 4, line 2, after "alkyl" insert --,--;
　　　　　line 6, delete second occurrence of "($C_2$-$C_{12}$) alkynylene";
　　　　　line 13, change "C=$CR_{33}$" to --C≡$CR_{33}$--; and
　　　　　line 43, change "kanoyloyloxy" to --kanoyloxy--.

Column 5, line 13, after "ethylene", change "." to --;--;
　　　　　line 14, change "$R_{53}$" to --$R_{52}$--;
　　　　　line 18, after "nitroso", change "." to --;--; change "$R_{43}$" to --$R_{42}$--;
　　　　　line 21, change "fonly" to --fonyl--;
　　　　　line 22, change "axido" to --azido--;
　　　　　line 25, change "$C_{10}$" to --$C_{30}$--;
　　　　　line 26, change "$C_{10}$" to --$C_{30}$--;
　　　　　line 30, change "straigh" to --straight--;
　　　　　line 47, change "$C_5$" to --$C_6$--;
　　　　　line 59, change "$R_{21}$" to --$R_{23}$--; change "$NR_{24}$COOO" to --$NR_{24}$COO--;
　　　　　line 60, change "SC" to --SO--; and
　　　　　line 63, change "unsturated" to --unsaturated--.

Column 6, line 7, after "acetoxy", insert --,--;

UNITED STATES PATENT AND TRADEMARK OFFICE
CERTIFICATE OF CORRECTION

PATENT NO. : 5,364,847
DATED : November 15, 1994
INVENTOR(S) : Fernand Labrie, et al.

It is certified that error appears in the above-indentified patent and that said Letters Patent is hereby corrected as shown below:

Column 6, line 34, change "$R_{51}$" to --$R_{61}$--;
         line 36, after "halogen," insert --lower alkyl--;
         line 38, change "Sa" to --Se--;
         line 55, change ")$_s$" to --)$_r$S(CH$_2$)$_s$--; change "(CH$_2$)$_r$SO(CH$_2$)$_r$SO(CH$_2$" to --(CH$_2$)$_r$SO(CH$_2$--;
         line 58, change "(CH)$_{2r}$CR$_{22}$OR$_{22}$(CH$_2$)$_{2s}$" to --(CH$_2$)$_r$CR$_{22}$OR$_{22}$(CH$_2$)$_s$--;
         line 60, change "moisty" to --moiety--; and
         line 68, change "whrein" to --wherein--.

Column 7, line 6, change "eing" to --being--; after "from" insert --0 to--;
         line 9, change "alkylsil" to --alkylsilyl--;
         line 11, change "$R_{11}$" to --$R_{21}$--;
         line 32, change "ethylens" to --ethylene--;
         line 55, change "carbonyl" to --carboxyl--; and
         line 67, change "(CH$_3$Se)" to --CH$_2$Se)--.

Column 8, line 17, change "$R_{33}$" to --$R_{22}$--;
         line 26, delete "13";
         line 31, change "SO$_3$" to --SO$_2$--;
         line 33, after "-S-,", insert ---SO-,--; and
         line 64, change "proges" to --proper--.

UNITED STATES PATENT AND TRADEMARK OFFICE
CERTIFICATE OF CORRECTION

PATENT NO. : 5,364,847
DATED : November 15, 1994
INVENTOR(S) : Fernand Labrie, et al.

It is certified that error appears in the above-indentified patent and that said Letters Patent is hereby corrected as shown below:

Column 9, line 4, change "brease" to --breast--;
line 18, change "$R_{14}$" to --$R_{16}$--;
line 20, change "aklynyl" to --alkynyl--; and, change "alkycarbonyl" to --alkylcarbonyl--.

Column 10, line 6, change "$R_{35}$" to --$R_{36}$--;
line 10, change "$R_5$" to --$R_6$--;
line 22, change "$A^2$" to --$A^1$--;
line 46, delete "13"; and
line 54, after "-S-,", insert ---SO-,--.

Column 11, line 5, change "$R_{25}$" to --$R_{26}$--; change "($C_5$" to --($C_6$--;
line 6, change "$NR_{25}$" to --$NR_{26}$--;
line 25, change "$A^{22}$" to --$A^{11}$--;
line 26, change "$R_{15}(\beta)$" to --$R_{16}(\beta)$--;
line 28, change "nitrole" to --nitrile--;
line 38, change "($C_3$-$C_{12}$)" to --($C_2$-$C_{12}$)--;
line 42, delete "($C_3$-$C_7$)cy-";
line 43, delete "cloalkyl"; and
line 48, change "($C_2$-$C_{10}$)" to --($C_1$-$C_{20}$)--.

Column 12, line 41, change "$R_{43}$" to --$R_{42}$--; and
line 64, change "helogeno" to --halogeno--.

UNITED STATES PATENT AND TRADEMARK OFFICE
CERTIFICATE OF CORRECTION

PATENT NO. : 5,364,847

DATED : November 15, 1994

INVENTOR(S) : Fernand Labrie, et al.

It is certified that error appears in the above-indentified patent and that said Letters Patent is hereby corrected as shown below:

Column 13, line 17, change "$X_{45}$" to --$X_{46}$--;
change "$Y_{45}$" to --$Y_{46}$--;
line 19, change "$Y_{45}$" to --$Y_{46}$--;
line 25, change "$Y_7$" to --$Y_{47}$--;
line 26, change "$Y_{37}$" to --$Y_{47}$--;
line 28, change "$R_{45}$" to --$R_{46}$--; and
line 56, change "$R_{33}$ to --$R_{22}$--.

Column 14, line 38, change "tests" to --testes--.

Column 15, line 17, change "sto" to --ste--; and
line 43, change "methylenestar" to --methylen-estra--.

Column 16, line 2, change "undecanemaide" to --undecanamide--;
line 15, change "0.063," to --0.063---;
line 22, change "undecanemaide" to --undecanamide--;
line 32, after "dried", insert --on anhydrous magnesium sulfate, filtered and evaporated to dryness--;
line 37, change "undecaneamide" to --undecanamide--;
line 45, change "alkamides" to --alkylamides--;
line 58, change "$R_3$" to --$R_2$--;
line 64, change "$C_3H_5CO$" to --$C_2H_5CO$--;
line 65, change "$C_6H_{23}CO$" to --$C_6H_{13}CO$--; and

UNITED STATES PATENT AND TRADEMARK OFFICE
CERTIFICATE OF CORRECTION

PATENT NO. : 5,364,847    Page 7 of 10
DATED : November 15, 1994
INVENTOR(S) : Fernand Labrie, et al.

It is certified that error appears in the above-indentified patent and that said Letters Patent is hereby corrected as shown below:

```
Column 16, line 66, change "(CH₃)CO" to --(CH₂)CO--.

Column 17, line 12, change "R₃" to --R₂--; and
          line 16, change "C₆H₃CO" to --C₆H₅CO--.

Column 18, line  3, change "Cl₃" to --Cl₂--; and
          line 31, change "CH₂" to --CH₃--; change
                   "d,1HJ" to --d,1H,J--;
          line 32, change "3H N" to --3H, N--; and
          line 60, after "6'-H", insert --)--.

Column 19, line  3, change "C₃₉" to --C₃₈--; and
          line 29, change "1250" to --1205--.

Column 20, line 19, change "J₃" to --J₂--.

Column 21, line 37, change "66⁵" to --Δ⁵--.

Column 22, line 48, change "96.4" to --96:4--.

Column 23, structure 10, line 1, change "OTHP" to
                         --THPO--;
          line 45, change "O₃" to --O₂--;
          line 61, change "CH-CH₂, CH₃" to
                   --CH-CH₂-CH₃--;
          line 63, change "Hz,1-C≡CH-)" to
                   --Hz,(-C=CH-)--;
          line 65, change "12,12" to --12,13--.
```

UNITED STATES PATENT AND TRADEMARK OFFICE
CERTIFICATE OF CORRECTION

PATENT NO. : 5,364,847　　　　　　　　　　Page 8 of 10
DATED　　　: November 15, 1994
INVENTOR(S) : Fernand Labrie, et al.

It is certified that error appears in the above-indentified patent and that said Letters Patent is hereby corrected as shown below:

Column 24, line 41, change "C$\underline{H}_3$CON" to --C$\underline{H}_2$CON--;
　　　　　　line 42, change "NC$\underline{H}_3$", second occurrence, to --NC$\underline{H}_2$--;
　　　　　　line 47, change "pentadeconic" to --pentadecenoic--;
　　　　　　line 59, change "pentadeconic" to --pentadecenoic--;
　　　　　　line 61, change "$\nu_{max}$" to --$\lambda_{max}$--.
　　　　　　line 63, change "-C$\underline{H}_3$C$\underline{H}_3$" to ---C$\underline{H}_2$C$\underline{H}_3$--;
　　　　　　line 67, change "C$\underline{H}_3$" to --C$\underline{H}_2$--.

Column 25, structure 12, above reaction arrow, change "1) LOA" to --1) LDA--;
　　　　　　line 41, change "p-hydroxypohenyl" to --p-hydroxyphenyl--.

Column 26, scheme 5 cont'd., line 57, on the line following "NBu$_3$", insert --3) HNR$_1$R$_2$--.

Column 27, line 46, change "CH1" to --HCl--.

Column 28, line 34, change "hyroxyl" to --hydroxyl--; and
　　　　　　line 46, change "speices" to --species--.

UNITED STATES PATENT AND TRADEMARK OFFICE
CERTIFICATE OF CORRECTION

PATENT NO. : 5,364,847
DATED : November 15, 1994
INVENTOR(S) : Fernand Labrie, et al.

It is certified that error appears in the above-indentified patent and that said Letters Patent is hereby corrected as shown below:

Column 29, line 2, change "-$CR_{22}OR_{22}$-" to ---$CR_{22}OR_{22}$,---;
  line 21, change "$NR_{24}CO$" to --$NR_{24}COO$--; and
  line 59, change "$AXR_{21},A_1$" to --$AXR_{21},A^1$--.

Column 30, line 6, change "$AXR_2$" to --$AXR_{21}$--;
  line 43, change "propoynyl" to --propynyl--;
  line 44, change "$C_{17}$" to --$C_7$--; and
  line 45, change "($C_3$-$C_7$)alkenyloxy" to --($C_3$-$C_7$)alkenoyloxy--.

Column 31, line 36, after "compound" insert --is:--.

Column 32, line 43, change "foregoin" to --foregoing--.

Column 33, line 21, change "$A_1$" to --$A^1$--;
  line 31, change "$AXR_2$" to --$AXR_{21}$--; and

UNITED STATES PATENT AND TRADEMARK OFFICE
CERTIFICATE OF CORRECTION

PATENT NO.    : 5,364,847
DATED         : November 15, 1994
INVENTOR(S)   : Fernand Labrie, et al.

It is certified that error appears in the above-indentified patent and that said Letters Patent is hereby corrected as shown below:

Column 33, line 38, change "cycloalkyenyl" to --cycloalkenyl--.

Signed and Sealed this

Eighth Day of October, 1996

Attest:

BRUCE LEHMAN

Attesting Officer      Commissioner of Patents and Trademarks